(12) United States Patent
Michaels

(10) Patent No.: US 7,930,926 B2
(45) Date of Patent: Apr. 26, 2011

(54) DETERMINATION OF PERMEABILITY FROM DAMPING

(75) Inventor: Paul Michaels, Boise, ID (US)

(73) Assignee: Boise State University, Boise, ID (US)

( * ) Notice: Subject to any disclaimer, the term of this patent is extended or adjusted under 35 U.S.C. 154(b) by 242 days.

(21) Appl. No.: 12/113,937

(22) Filed: May 1, 2008

(65) Prior Publication Data

US 2009/0133476 A1 May 28, 2009

Related U.S. Application Data

(60) Provisional application No. 60/915,346, filed on May 1, 2007.

(51) Int. Cl.
*G01N 15/08* (2006.01)
(52) U.S. Cl. .......... 73/38; 73/37; 73/152.05; 73/152.06; 73/152.08
(58) Field of Classification Search .............. 73/37, 38, 73/152.05, 152.06, 152.08, 570, 594
See application file for complete search history.

(56) References Cited

U.S. PATENT DOCUMENTS

| | | | | |
|---|---|---|---|---|
| 3,935,745 A | * | 2/1976 | Jonell et al. | 73/704 |
| 4,150,578 A | * | 4/1979 | Swartz | 73/725 |
| 4,332,172 A | * | 6/1982 | Torstensson | 73/707 |
| 4,449,208 A | * | 5/1984 | Moeckel et al. | 367/30 |
| 4,751,688 A | | 6/1988 | Paulsson | |
| 4,783,771 A | | 11/1988 | Paulsson | |
| 4,805,725 A | | 2/1989 | Paulsson | |
| 5,142,500 A | * | 8/1992 | Yamamoto et al. | 367/57 |
| 5,796,678 A | * | 8/1998 | Pisetski | 367/38 |
| 5,804,715 A | * | 9/1998 | Bennett | 73/170.32 |
| 6,269,311 B1 | * | 7/2001 | Berryman | 702/18 |
| 6,374,186 B1 | * | 4/2002 | Dvorkin et al. | 702/18 |
| 6,498,989 B1 | * | 12/2002 | Pisetski et al. | 702/14 |
| 6,571,605 B2 | * | 6/2003 | Johnson | 73/38 |
| 7,136,757 B2 | * | 11/2006 | Goloshubin et al. | 702/17 |
| 2003/0140690 A1 | * | 7/2003 | Faybishenko | 73/152.18 |
| 2003/0217588 A1 | * | 11/2003 | Jalbert et al. | 73/38 |
| 2005/0177309 A1 | * | 8/2005 | Sri Ranjan et al. | 702/2 |

OTHER PUBLICATIONS

Paul Michaels, "Relating Damping to Soil Permeability", American Society of Civil Engineers, International Journal of Geomechanics, vol. 6, No. 3, May 2006.*
M.A. Biot, "Theory of Propagation of Elastic Waves in a Fluid-Saturated Porous Solid. I. Low-Frequency Range", The Journal of The Acoustical Society of America, Mar. 1956, pp. 168-178, vol. 28, No. 2, USA.

* cited by examiner

*Primary Examiner* — David A. Rogers
(74) *Attorney, Agent, or Firm* — Pedersen and Company, PLLC; Ken J. Pedersen; Barbara S. Pedersen

(57) ABSTRACT

Permeability of a fluid through a saturated material is determined by measuring the dynamic response of that saturated material to shaking vibrations and/or shear wave propagation, and then mapping the dynamic response (preferably, viscoelastic stiffness and damping properties) to an invented model (called "KVMB") that yields the property of permeability. The preferred embodiments may use shear waves, inertial effects, and/or transmission effects, but preferably not compression, to force fluids through the pores. The mapping preferably predicts two possible mappings to permeability, coupled and uncoupled. The preferred methods are both internally consistent and directly related to known laws of physics rather than dependent on empirical calibrations. In use, for example, one may use a porosity log (conventional neutron or sonic) and recordings of SH-waves to obtain damping ratio, followed by locating of the damping ratio on a KVMB map that depends on porosity, and choosing of one of the two possible permeabilities indicated by the mapping, wherein the best choice is typically the largely coupled case.

14 Claims, 25 Drawing Sheets

Two alternative dynamic representations of a soil or rock

Figure 1: Two alternative dynamic representations of a soil or rock

Figure 2: Solving for KVMB dashpots given KV damping ratio

Max. Ambient Pressure:   12,000 psi (73 MPa)
Max. Ambient Temperature:   350°F (175°C)
Source Wireline Length:   20,000 ft (6,100 m)
Radiation Patterns
Axial Vibrator
(1996)
Radial Vibrator
(1997)
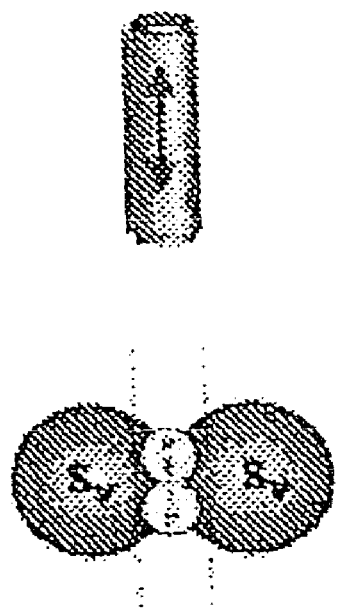
Axial Point Force
(Well Side View)
Radial Point Force
(Well Top View)
Figure 4

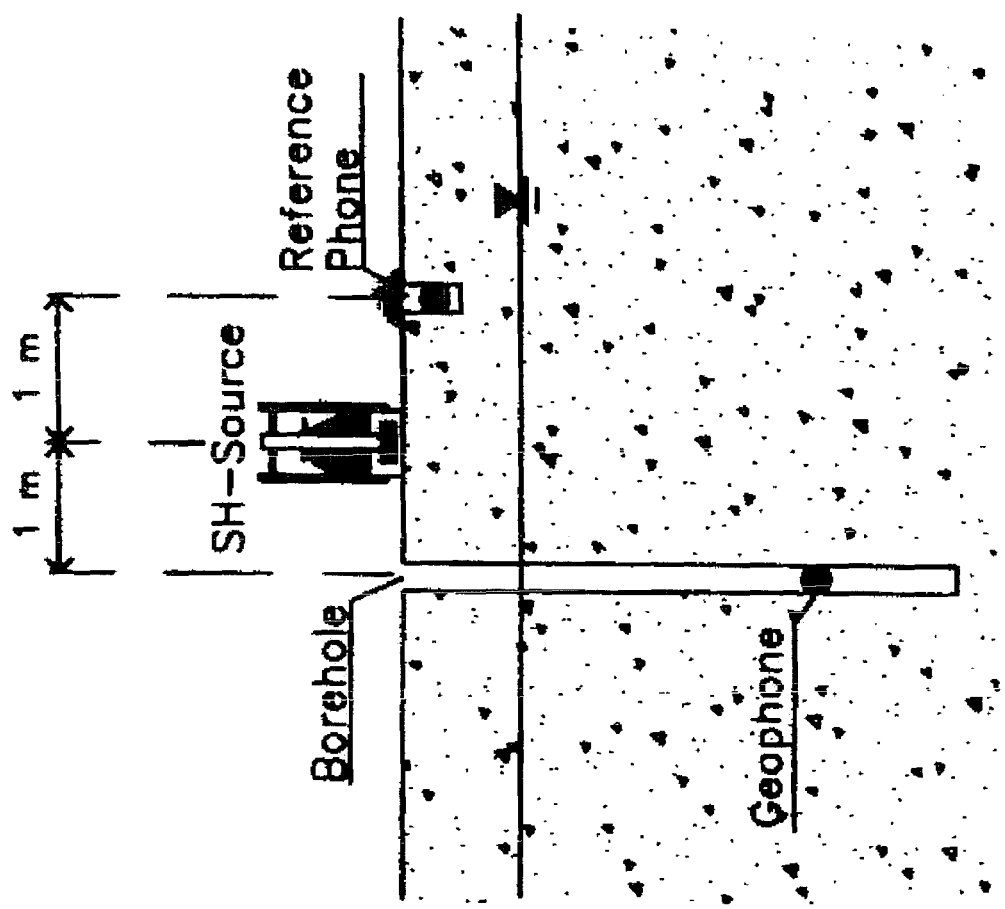
FIG. 5  Typical Down-Hole Experiment Shown In Cross Section

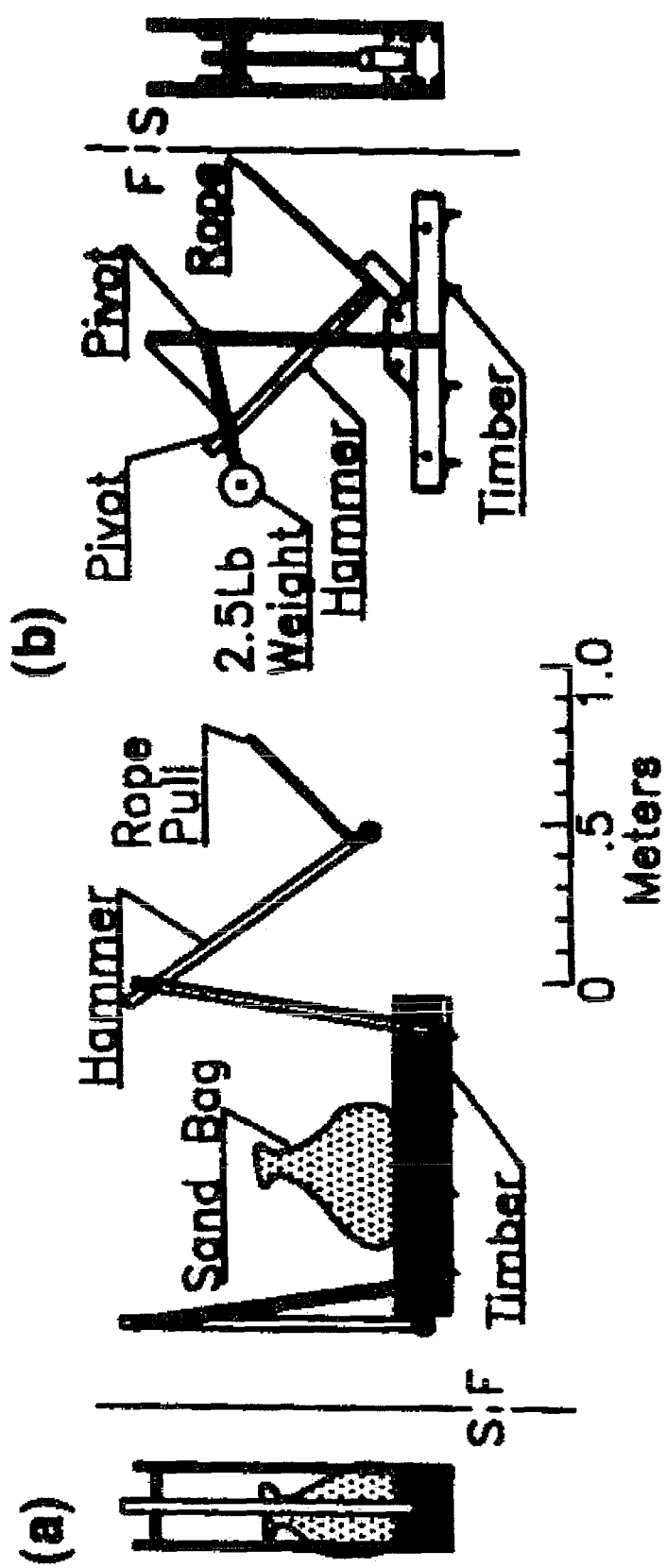
FIG. 6 SH-Wave Source Designs: (a) Horizontal Hammer Blow Source with Hold-Down Weight; (b) Inclined Hammer Source (135° from Vertical) Nailed to Soil

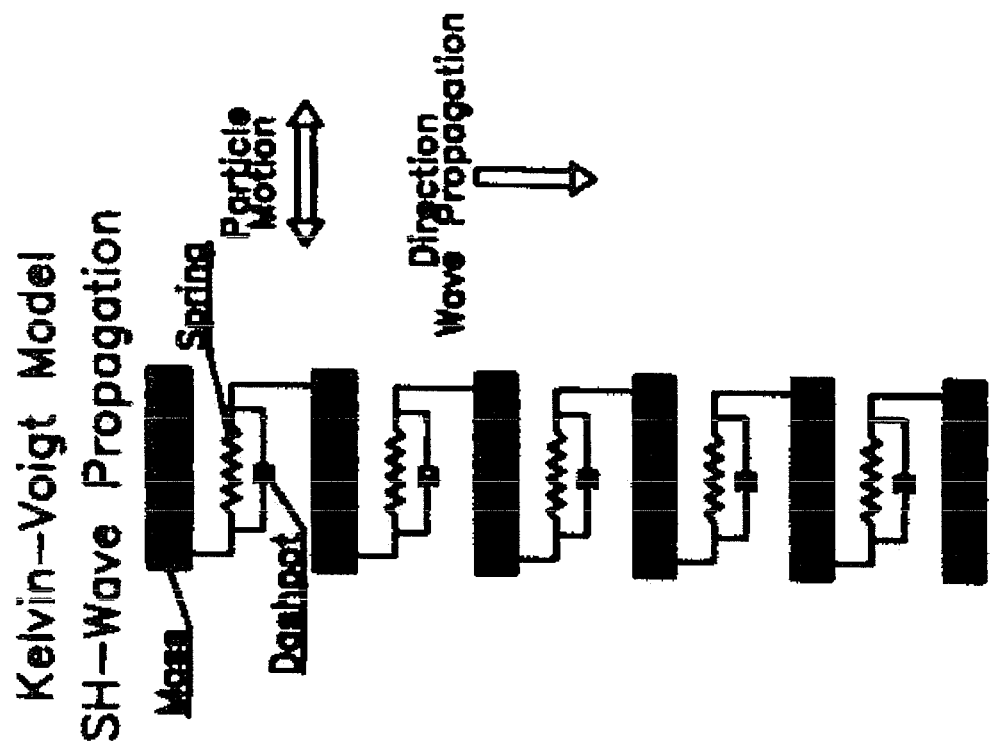
FIG. 7 Discrete Realization of Kelvin-Voigt Soil Model, Consisting of a Chain of Spring, Dashpot, and Mass Elements

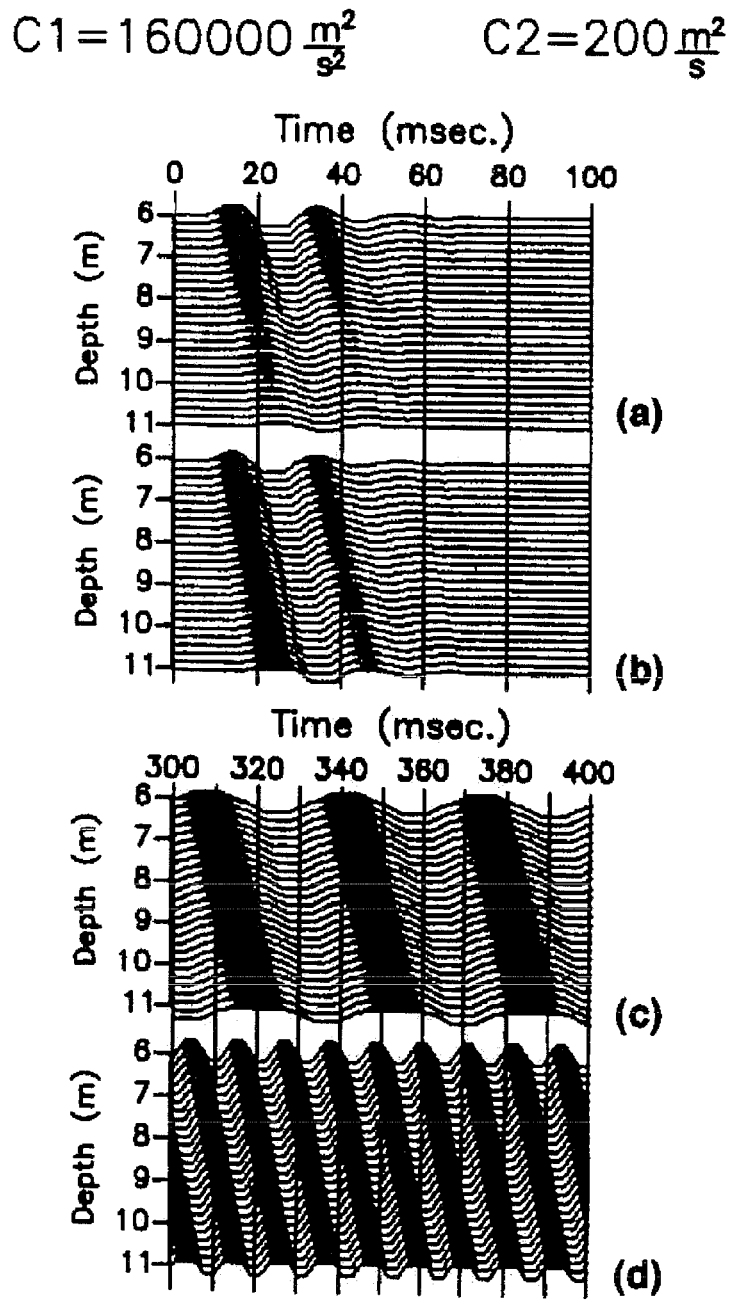
FIG. 8 Finite Difference Synthetic Data Used to Test the Software: (a) True Amplitude Display after Addition of Spherical Divergence Effects; (b) Rescaled Data to Permit Viewing of Waveform; (c) Velocity of 30 Hz Filtered Version; (d) 90 Hz Filtered Version

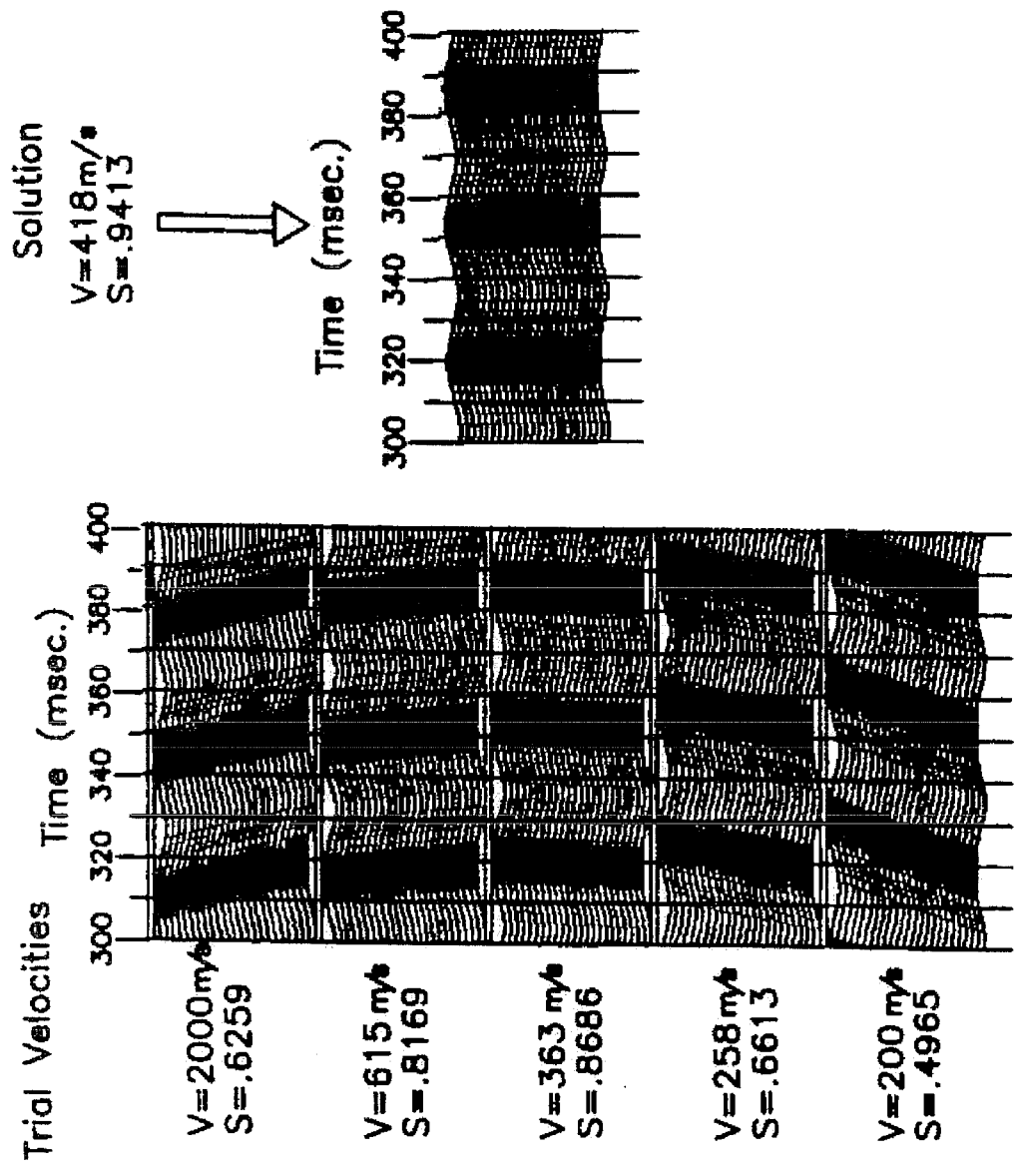
FIG. 9 Synthetic Data Velocity Analysis by Semblance (30 Hz at 6–11 m Depth)

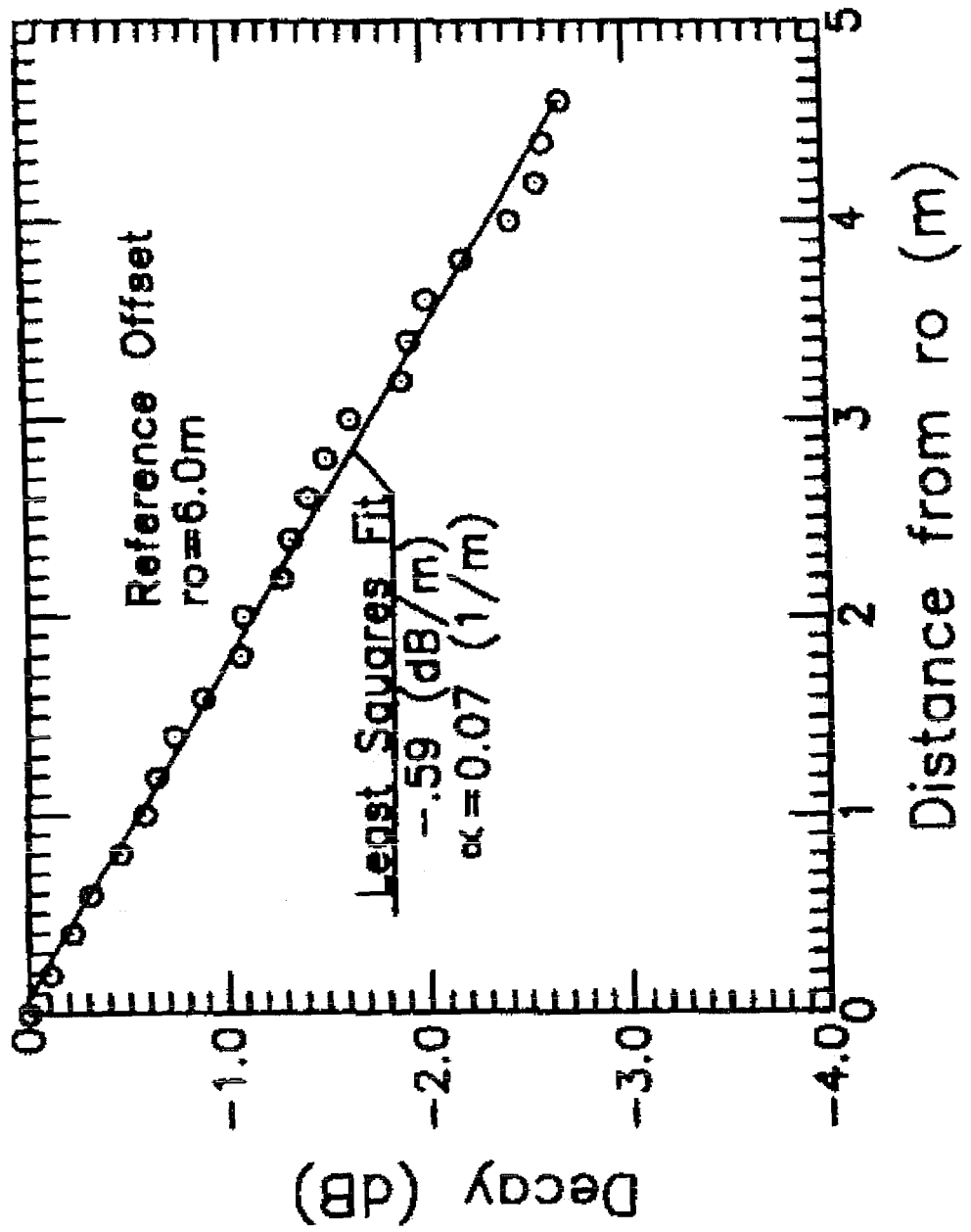
FIG. 10 Measurement of Synthetic Data Amplitude Decay (30 Hz)

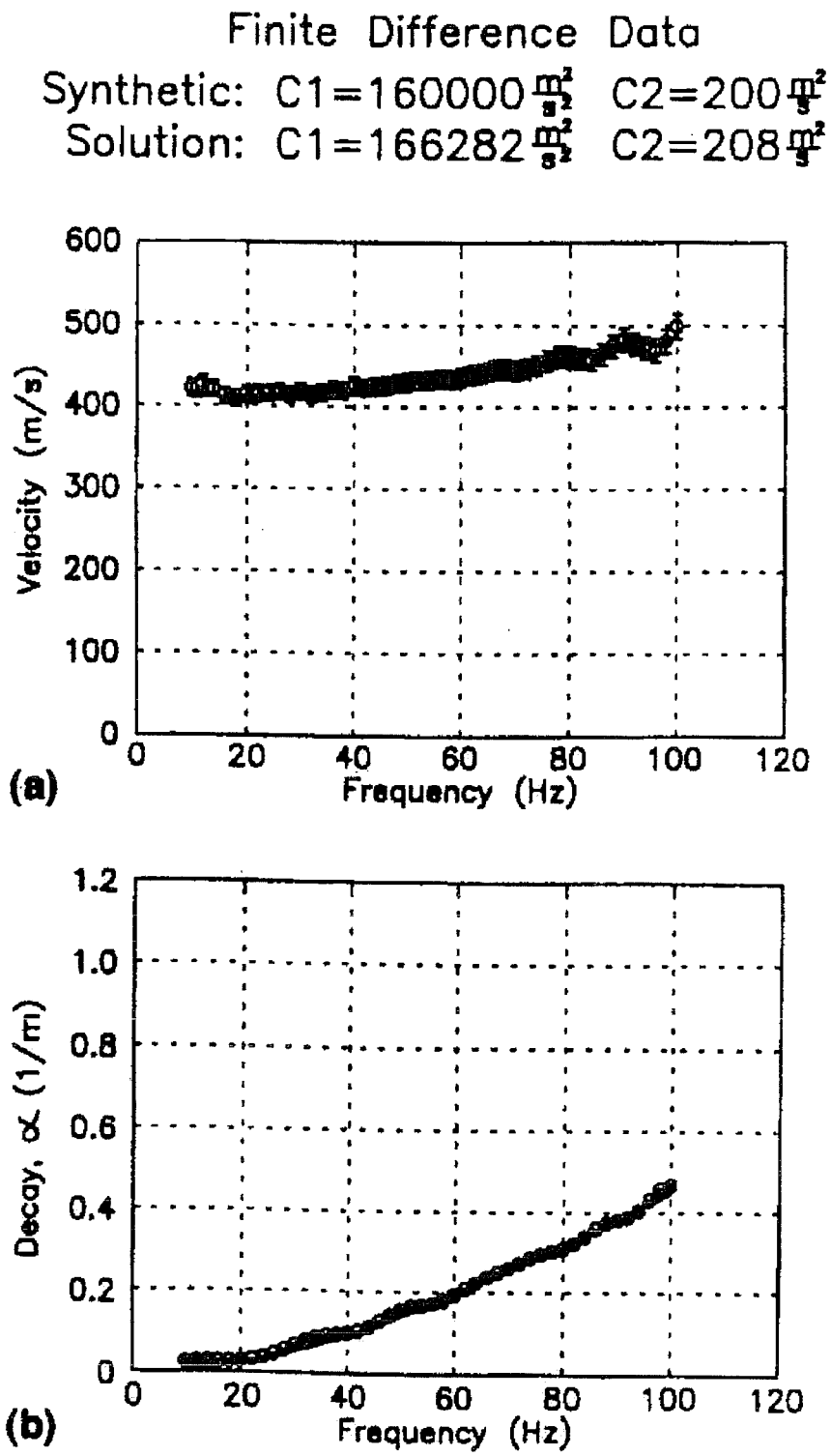
FIG. 11 (a) Measured Velocity Dispersion of Synthetic Data; (b) Amplitude Decay of Synthetic Data

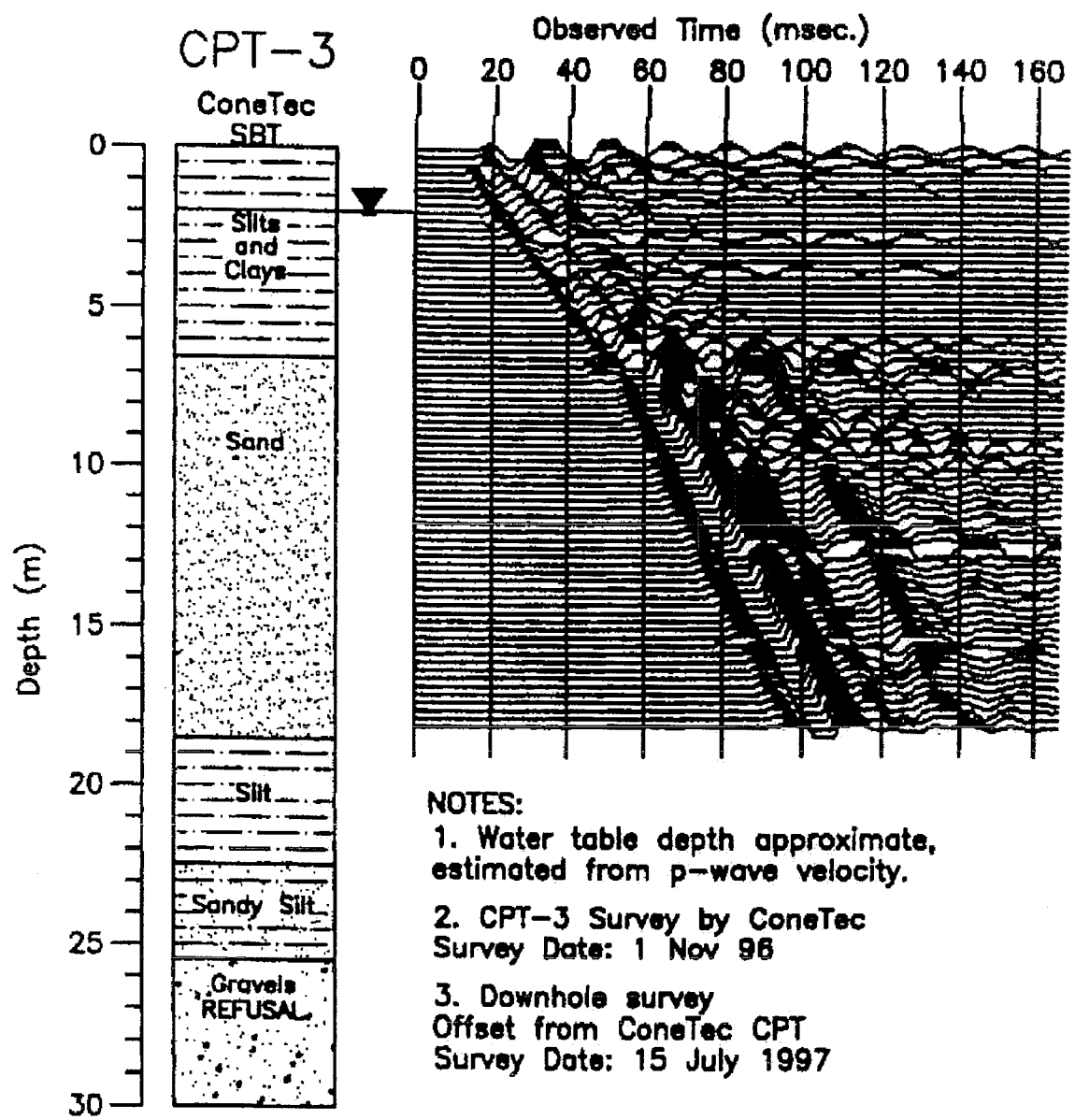
FIG. 12 Down-Hole SH-Wave Field Data from Logan, Utah, Site

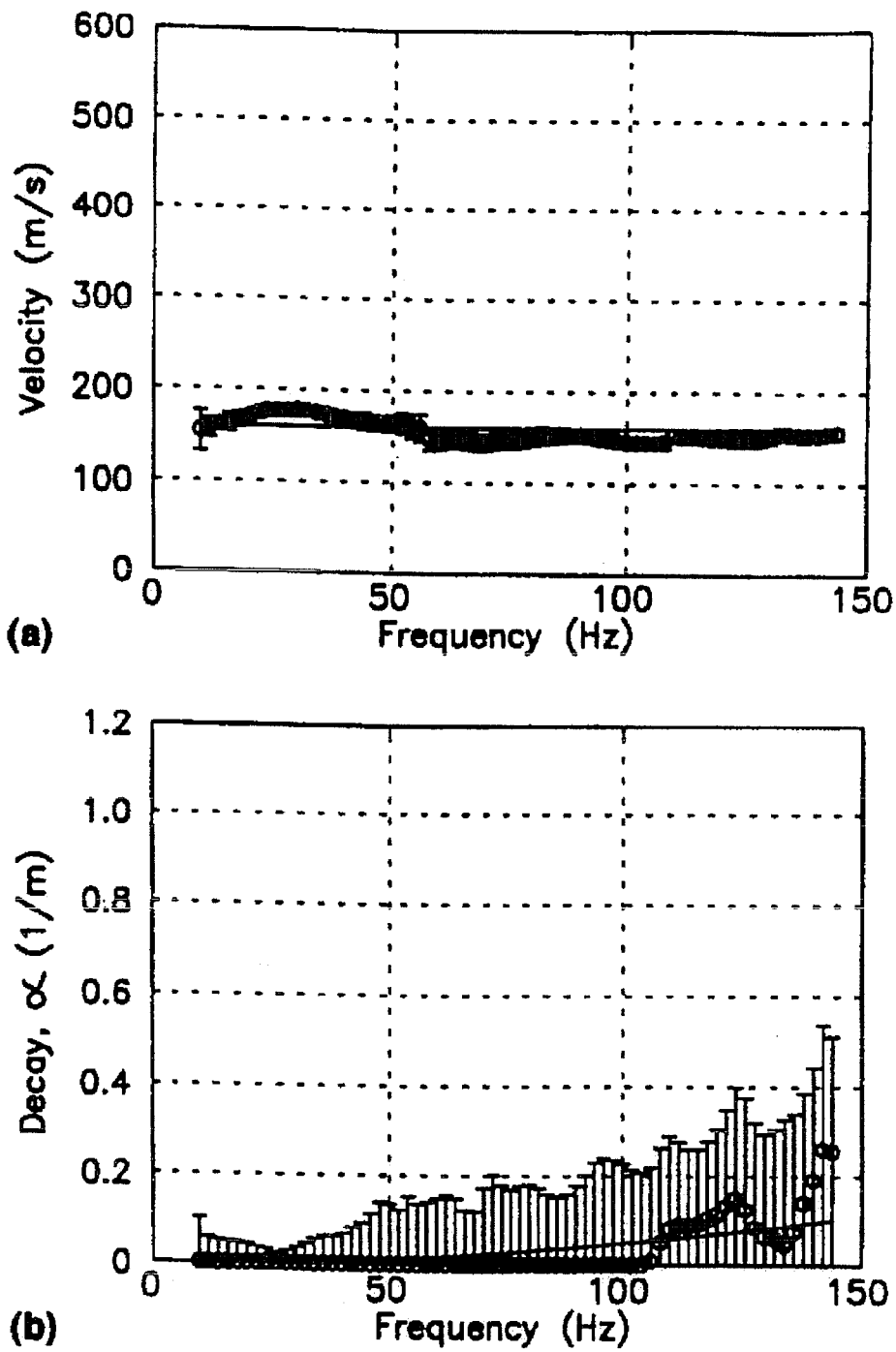
FIG. 13 GeoLogan SH-Wave Data (2–7 m): (a) Measured Velocity Dispersion from Silt Interval in Utah Data; (b) Amplitude Decay from Silt Interval in Utah Data

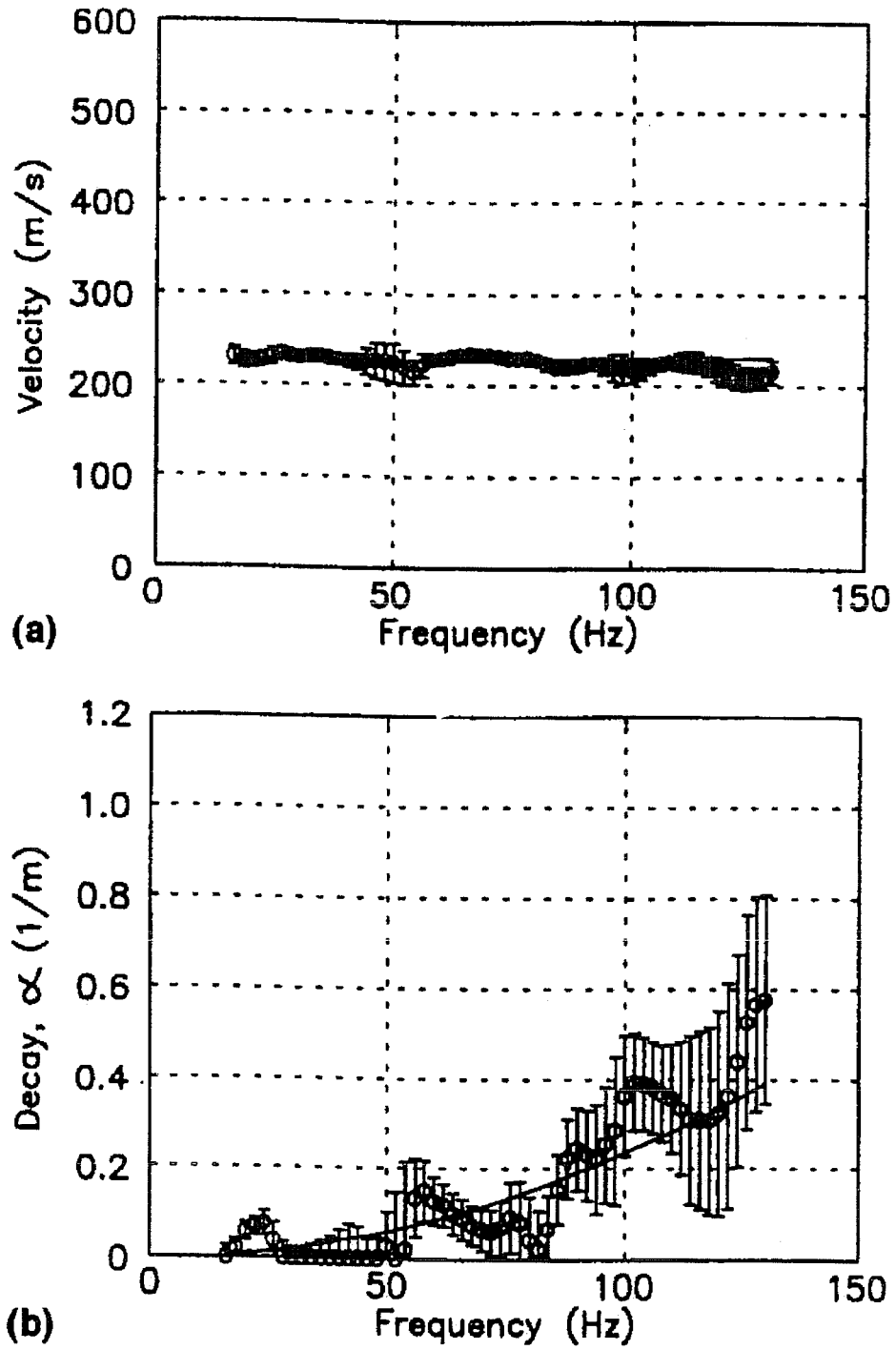
FIG. 14 GeoLogan SH-Wave Data (8–13 m): (a) Measured Velocity Dispersion from Sand Interval in Utah Data; (b) Amplitude Decay from Sand Interval in Utah Data

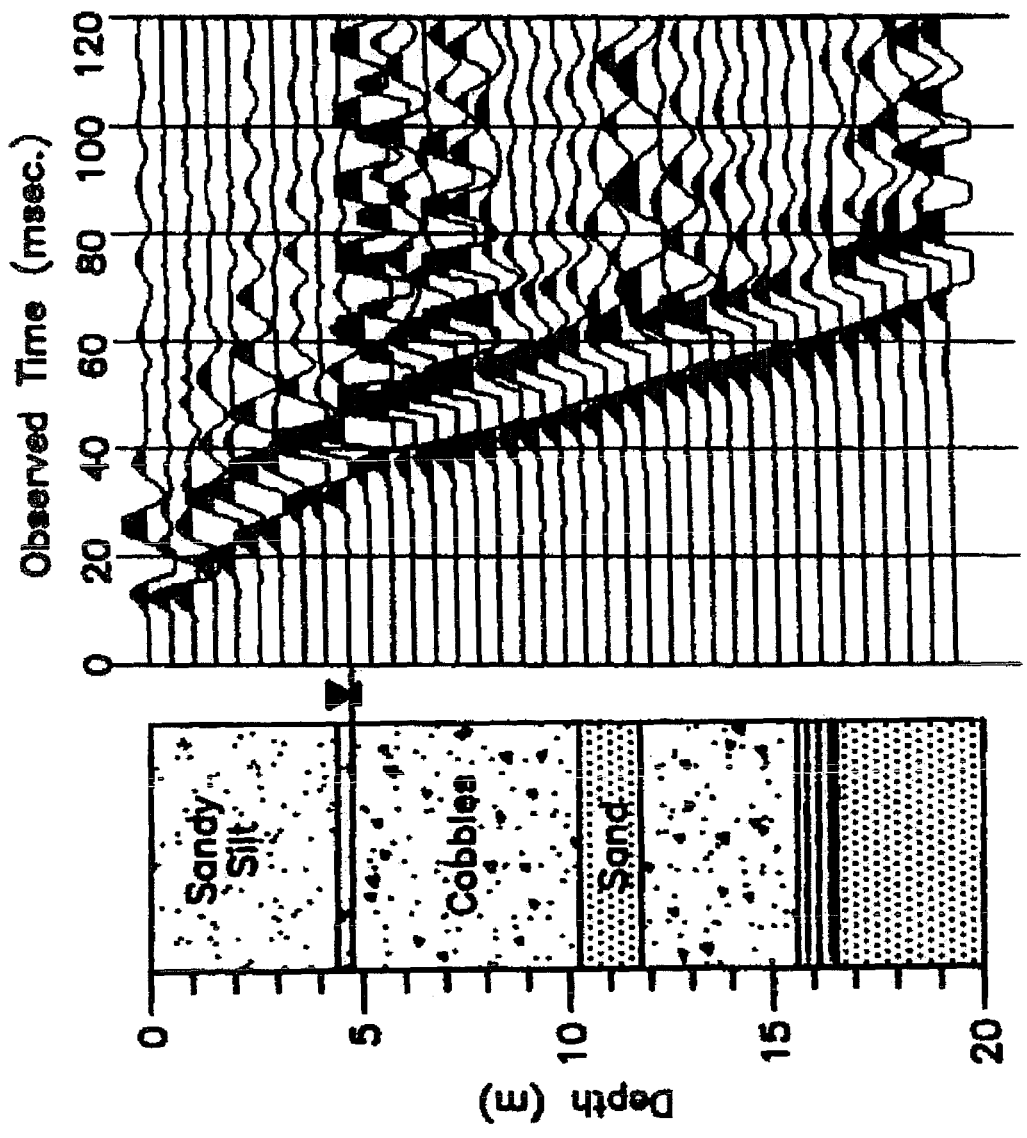
FIG. 15 Down-Hole SH-Wave Field Data from Boise, Idaho, Site

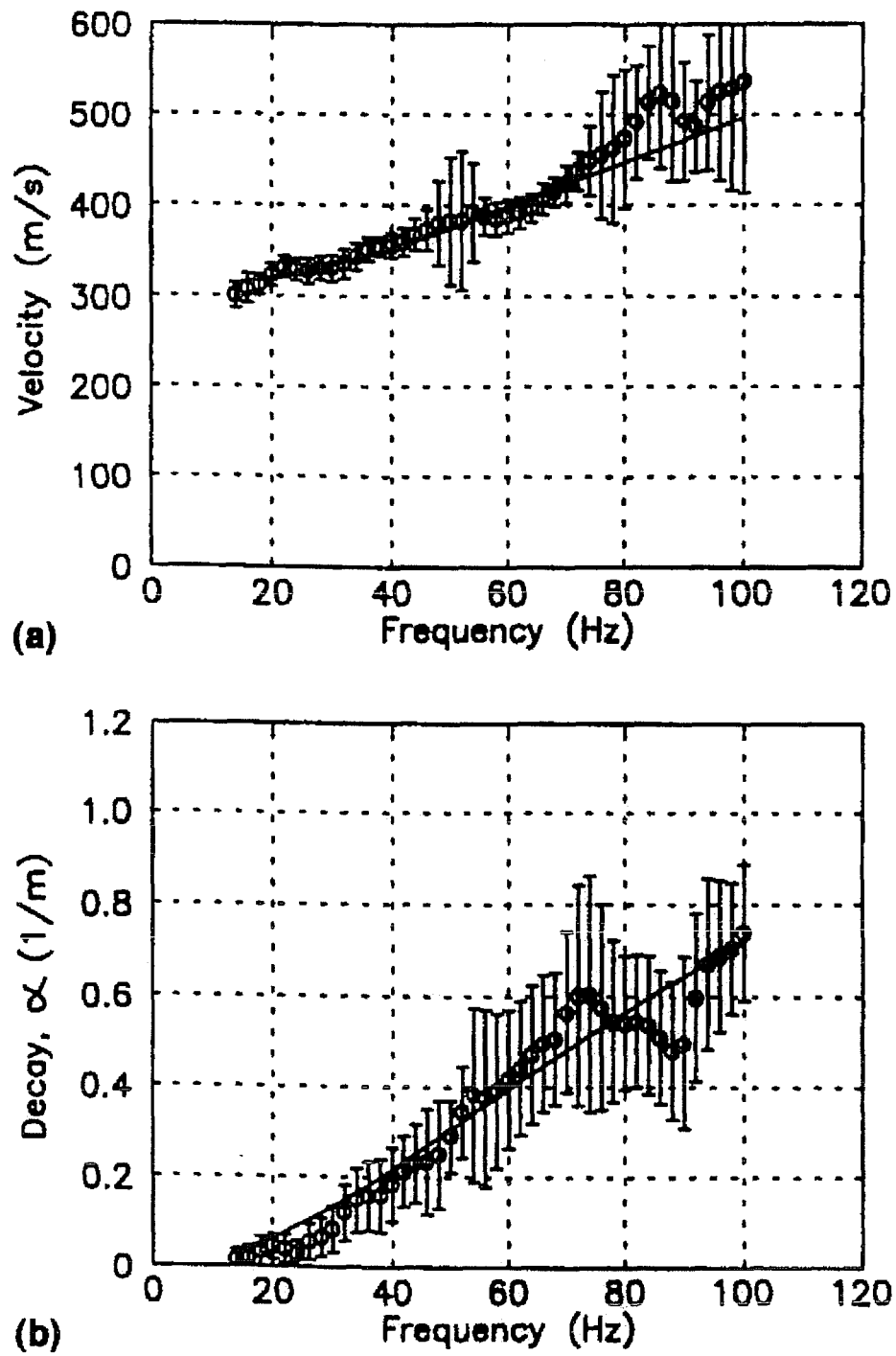
FIG. 16 Idaho SH-Wave Data (5–10 m): (a) Measured Velocity Dispersion from Upper Interval (5–10 m) in Idaho Data; (b) Amplitude Decay from Upper Interval in Idaho Data

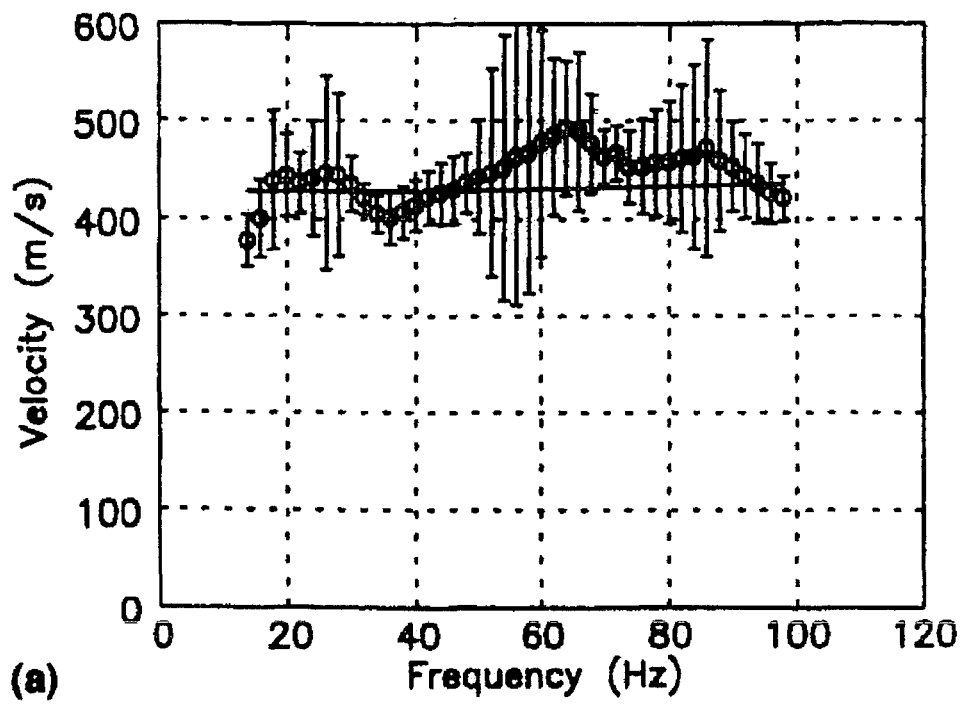
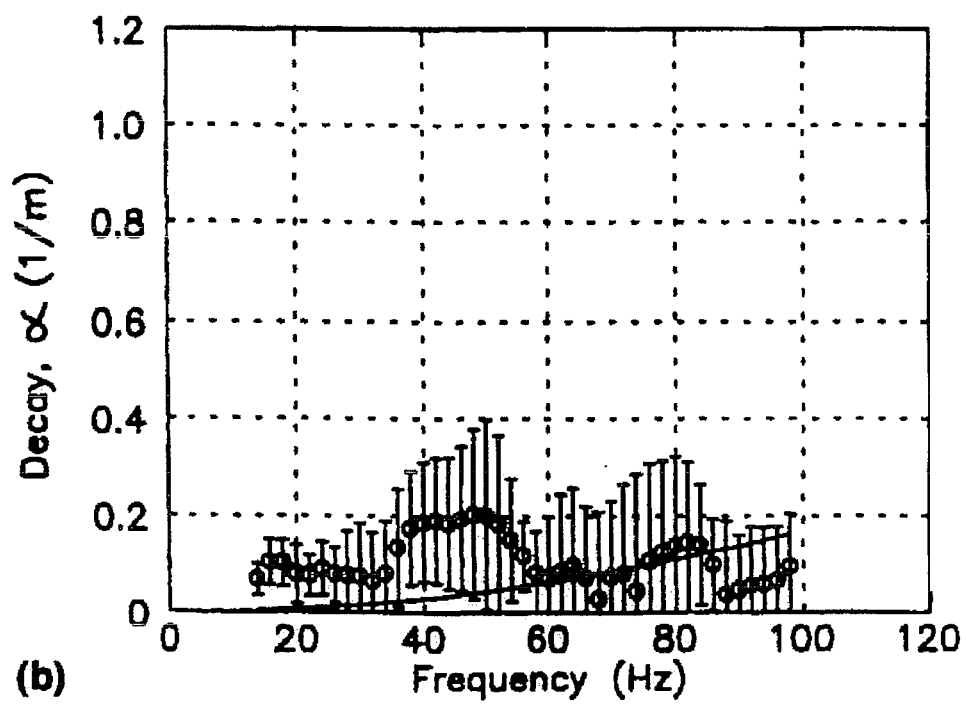
FIG. 17 Idaho SH-Wave Data (10–5 m): (a) Measured Velocity Dispersion from Deeper Interval (10–15 m) in Idaho Data; (b) Amplitude Decay from Deeper Interval in Idaho Data

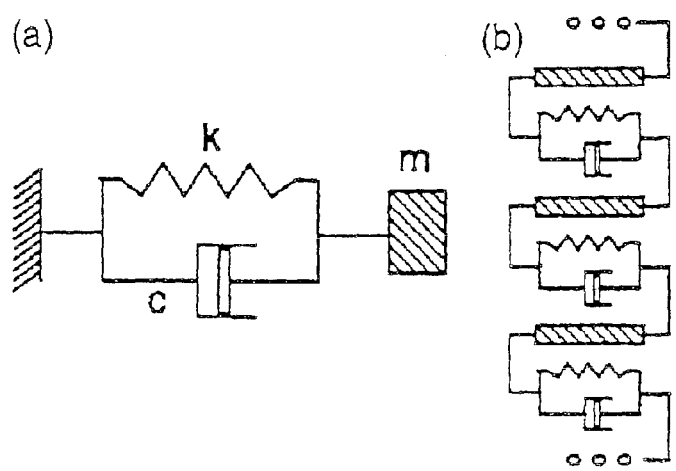
Fig. 18. Kelvin–Voigt soil representation for: (a) vibrator; (b) wave assemblage

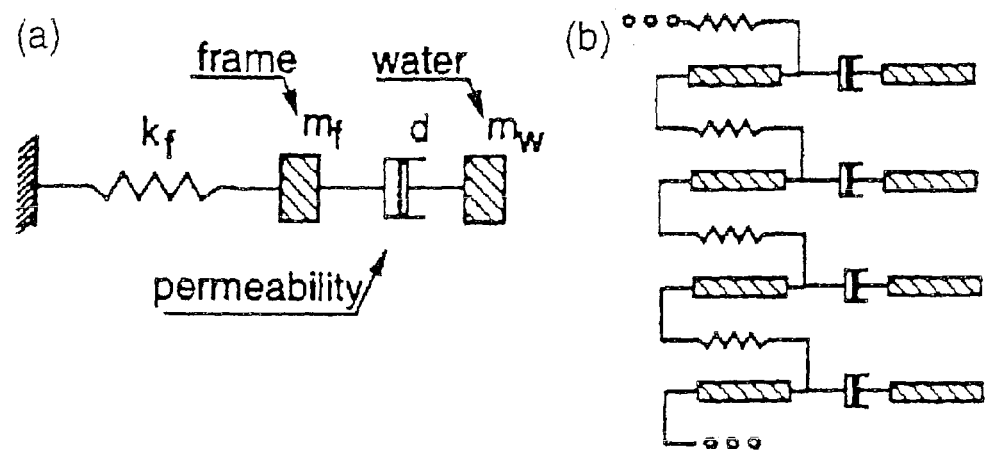
Fig. 19. Kelvin–Voigt–Maxwell–Biot soil representation for: (a) vibrator; (b) wave assemblage

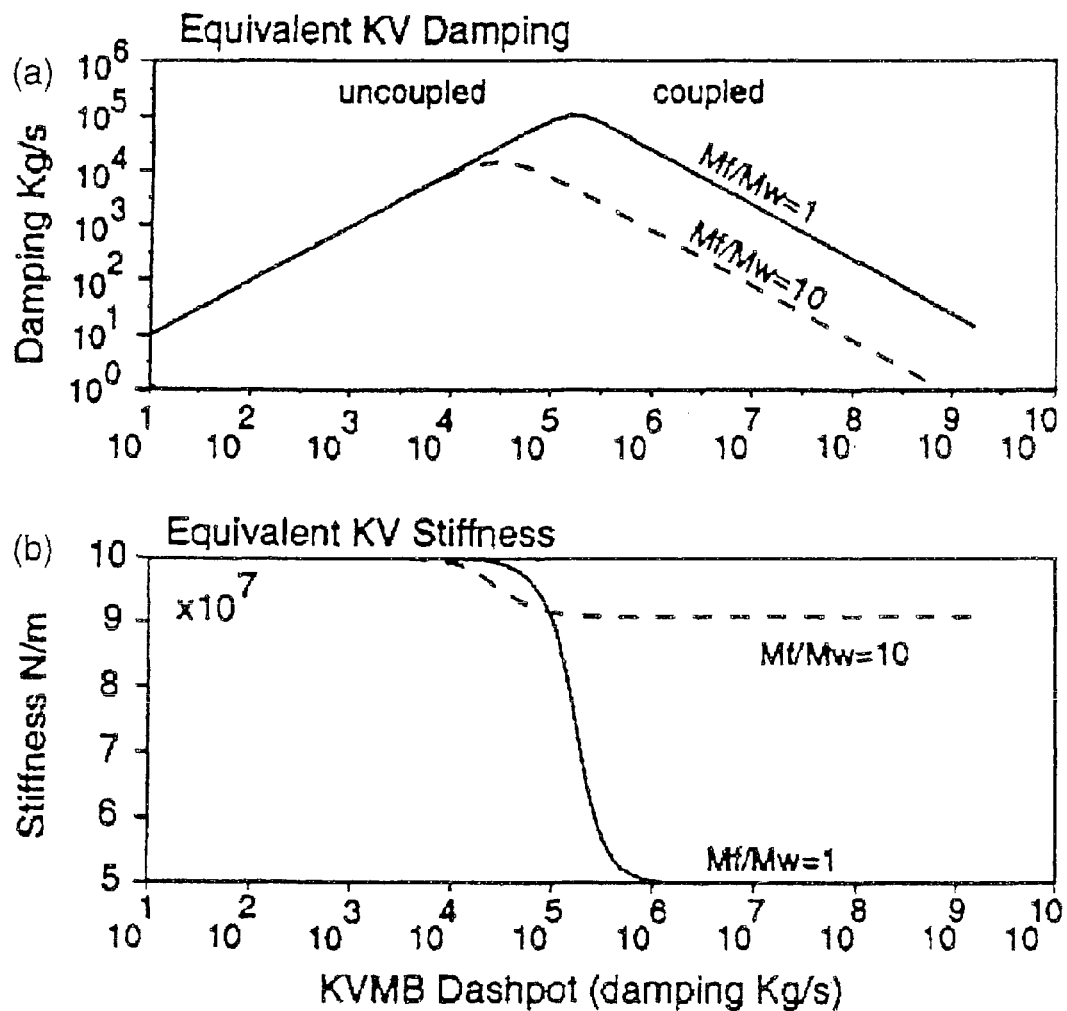
Fig. 20. Equivalent KV (a) damping; (b) stiffness for a KVMB thought experiment

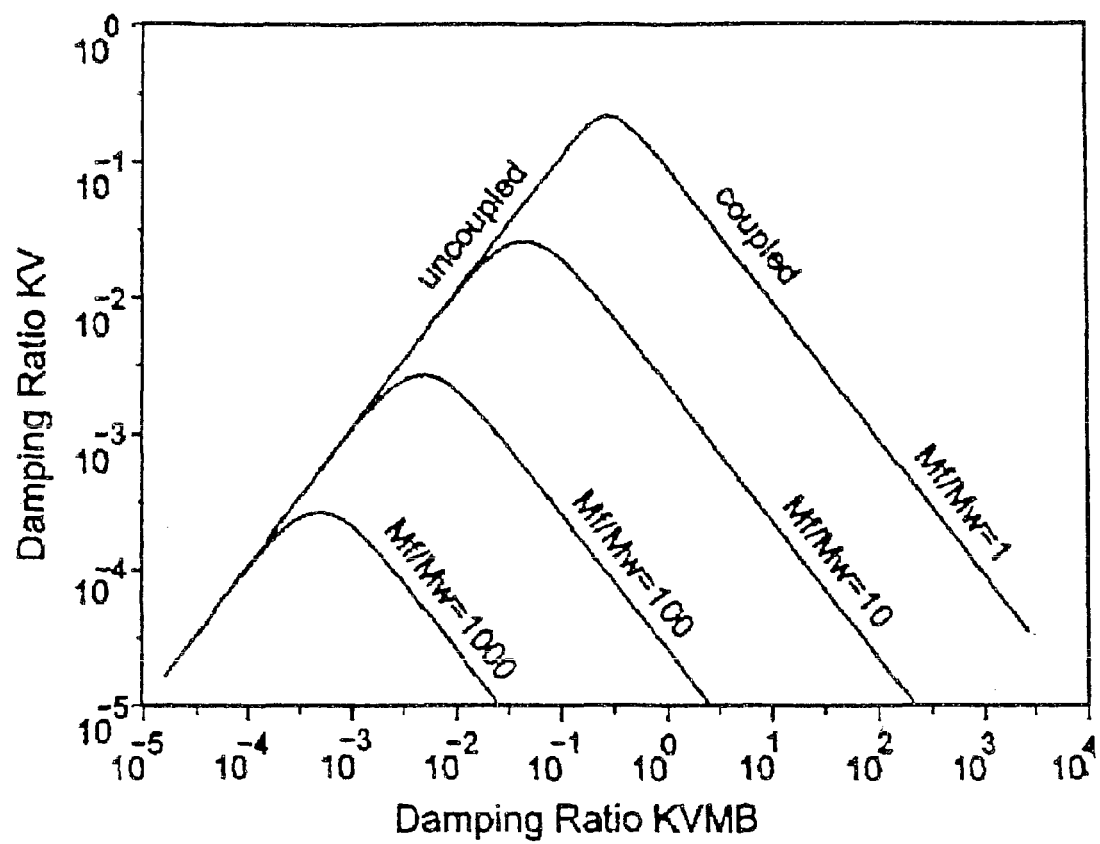
Fig. 21. Equivalent KV damping ratio as function of KVMB damping ratio for different mass ratios

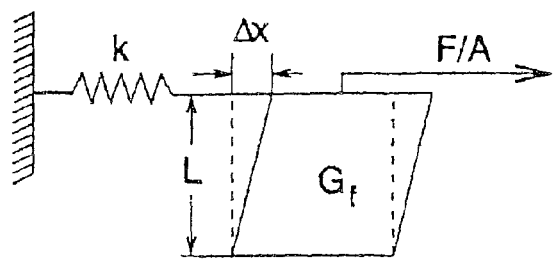
Fig. 22. Determining lumped spring stiffness from soil element's shear modulus, $G_f$

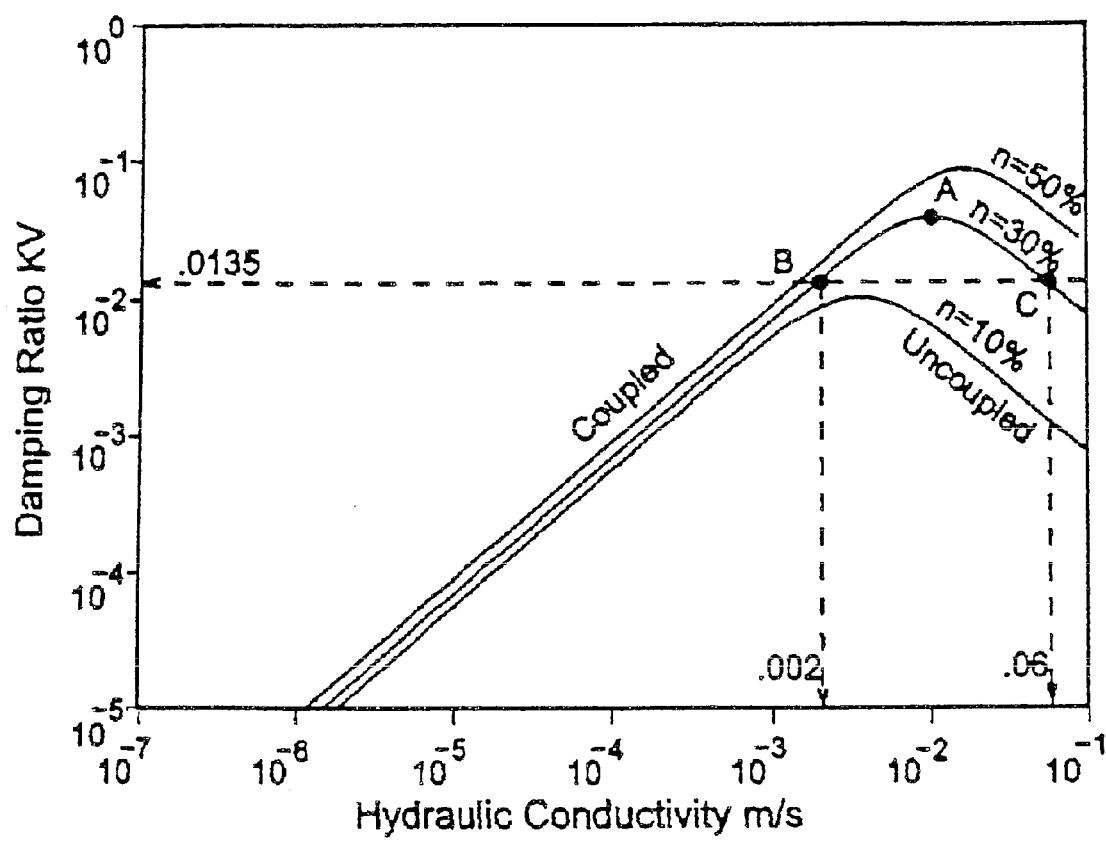
Fig. 23. Equivalent KV damping ratio as function of hydraulic conductivity at 50 Hz for different porosities

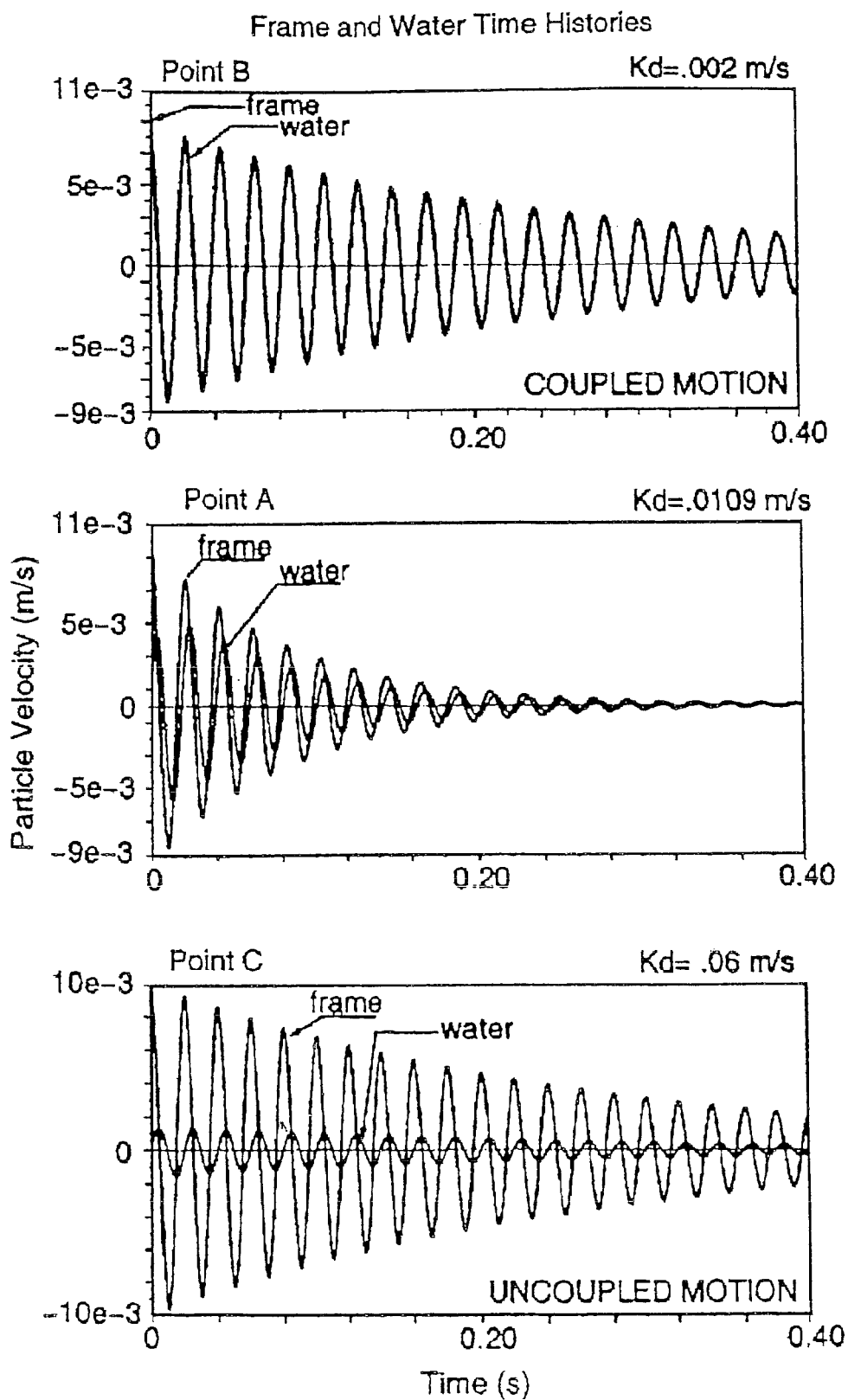
Fig. 24. Frame and water time histories corresponding to points $A$, $B$, and $C$ of Fig. 6

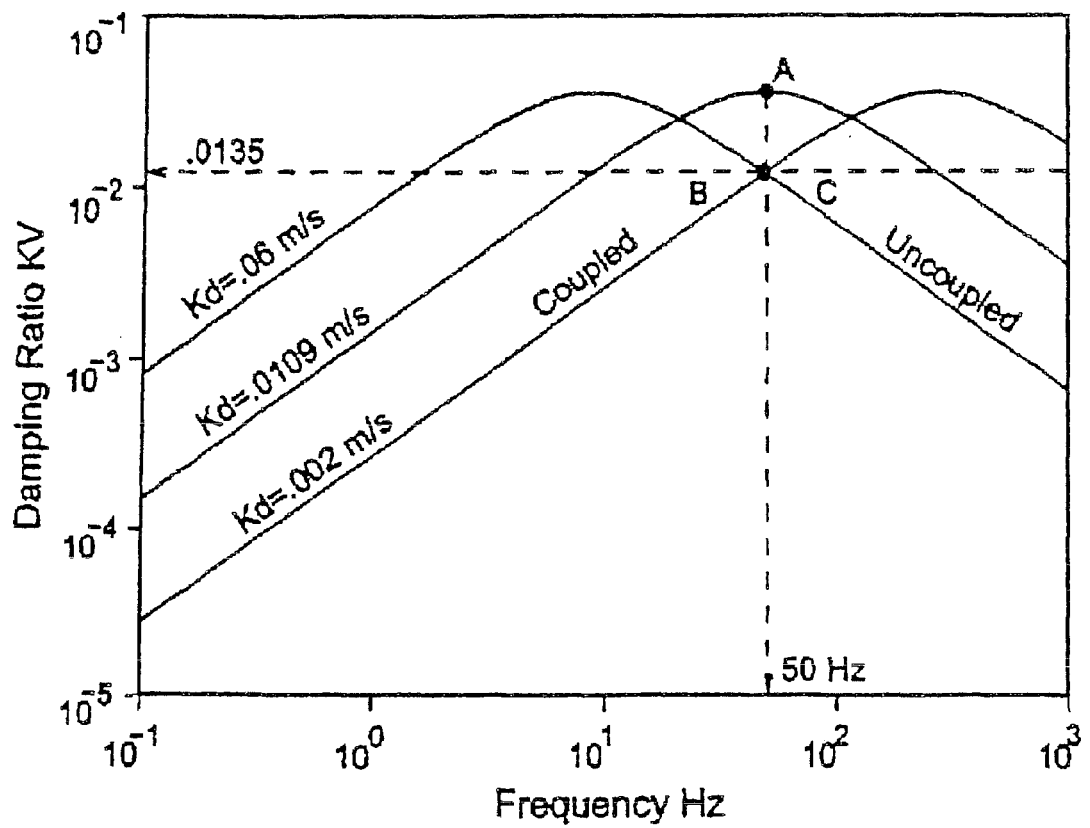
Fig. 25. Equivalent KV damping ratio as function of natural frequency for porosity of 30% for different hydraulic conductivities corresponding to points A, B, and C of Fig. 6

DETERMINATION OF PERMEABILITY FROM DAMPING

This application claims priority of Provisional Application Ser. No. 60/915,346, filed May 1, 2007, and entitled "Determination of Permeability From Damping," which is hereby incorporated by reference.

Early work on this matter was done with funding from U.S. Army Grant DA AH04-96-1-0318.

BACKGROUND OF THE INVENTION

1. Field of the Invention

The invention relates to methods, apparatus, and/or programming code means for determining the permeability of a fluid through a saturated material by measuring the dynamic response of that saturated material to shaking vibrations or shear wave propagation, and mapping data from said dynamic response to an invented alternative constitutive model that yields the property of permeability. Permeability may be described generally as the ease with which fluids can move through rock, soil, or other earth materials, and, therefore, the invented procedures, apparatus, and/or programming code means may be applied in oil well production, soil improvement, contaminated soils treatment, water well production, and/or landfill waste disposal, for example.

2. Related Art

Current non-seismic methods of permeability determination are limited to either laboratory tests (constant head or falling head), or to well tests like draw-down flow testing or drill stem testing in oil wells. The laboratory tests are restricted to small sample volumes and are not able to evaluate large samples with large grain sizes (ie: cobbles). Drawdown and other well flow tests are subject to skin affects and alterations of permeability within the invaded zone; for example, drilling muds can clog the formation in a zone near the borehole and lead to underestimation of permeability.

A number of existing seismic methods have been proposed in the prior art, however, their mathematical representations and procedures are different from those used in embodiments of the present invention. Such prior proposed methods can be quite complex, especially in the area of viscous representations, for example, the complex shear modulus. If a non-viscous "effective viscosity" is employed, it results in a complex modulus with a constant imaginary part. "Effective viscosity" is a concept that has its origins in past work with air saturated samples or seismic data of inadequate bandwidth; there are no materials know to possess "effective viscosity". The preferred embodiments, on the other hand, comprise "truly viscous" representations (frequency dependent imaginary part for the shear modulus opposed to a constant) rather than "effective viscosity."

One example of prior methods in the patent literature is Yamamoto, et al., (U.S. Pat. No. 5,142,500, 1992), which describes "Non-destructive method of measuring physical characteristics of sediments." Yamamoto is a cross-well-specific patent, uses hydrophones and compressional waves, does not distinguish between coupled and uncoupled motion, and is for P-waves (not S-waves). The preferred embodiments of the present invention, on the other hand, may use shear waves and inertial effects, but not compression, to force fluids through the pores.

Another example of prior methods in the patent literature is Goloshubin, et al. (U.S. Pat. No. 7,136,757, 2006), which describes "Frequency-dependent processing . . . fluid saturated reservoirs." Goloshubin is based on reflected P-waves, whereas the preferred embodiments of the present invention use shear-waves and transmission effects.

Further differences between preferred embodiments of the invention and the prior art may be found in the area of mapping of viscosity to permeability, and in that the present invention preferably predicts two possible mappings to permeability, coupled and uncoupled. Unlike prior art seismic methods known to the inventor, the methods of the preferred embodiments are both internally consistent and directly related to known laws of physics rather than dependent on empirical calibrations.

Further objects of some embodiments of the invention may comprise: sensing beyond the invaded zone, via shear-wave damping methods; extension to non-invasive applications; or applications for shallow, near-surface engineering problems, for example, comprising Love wave inversion for permeability.

These, and/or other, features and objects may be realized by embodiments of the invention, as will be understood by one of skill in the art after viewing the following description and attached Figures.

SUMMARY OF THE INVENTION

The present invention relates to a procedure, apparatus, and/or programming for determining the permeability of a fluid through a saturated material by measuring the dynamic response of that saturated material to shaking vibrations and/or shear wave propagation. Using embodiments of the invention, viscoelastic stiffness and damping properties, which may be determined from existing methods and hardware for creating said vibrations or shear waves, are mapped to an invented alternative constitutive model (named "KVMB" by the inventor) that yields/determines the property of permeability. Said mapping comprises projection of the problem to a decoupled basis.

Embodiments of the present invention may comprise apparatus and methods, currently commercially available, for physically testing the dynamic response of saturated material to shaking vibrations or shear wave propagation, and may comprise the computer/electronics apparatus and computer code to map said dynamic response(s) to the KVMB model, so that the petrophysical property of permeability may be determined. Apparatus and methods for performing said physical testing may include cross-well, down-hole, resonant column, down-hole vibrators, surfaces sources, geophone arrays, and/or Visual Sample Plan (VSP), for example.

In use, for example, one may use a porosity log (conventional neutron or sonic) and recordings of SH-waves to obtain damping ratio, followed by locating of the damping ratio on an embodiment of the invented KVMB map that depends on porosity, and choosing of one of the two possible permeabilities indicated by the mapping, wherein the best choice is typically the largely coupled case.

BRIEF DESCRIPTION OF THE DRAWINGS

FIG. 4 is a schematic portrayal of example radiation patterns of equipment that may be used in physical testing to obtain data in some embodiments of the invention.

FIG. 5 is one example of a typical down hole experiment shown in cross section, such as used in Example A.

FIGS. 6A and B are portrayals of the inventor's SH wave source designs, as discussed in Example A: FIG. 6A being horizontal hammer blow source with hold down weight, and FIG. 6B being an inclined hammer source (135 degrees from vertical) nailed to soil.

FIG. 7 is a discrete realization of Kelvin/Voigt soil model consisting of a chain of spring, dashpot and mass elements, as discussed in Example A.

FIGS. 8A-C illustrate finite difference synthetic data used to test the software, as discussed in Example A, wherein FIG. 8A portrays the true amplitude display after spherical divergence effects have been added, FIG. 8B portrays resealed data to permit viewing of the waveform, FIG. 8C portrays velocity of 30 Hz filtered version, and FIG. 8D portrays 90 Hz filtered version. It may be noted that the velocity of the 30 Hz (FIG. 8C) filtered version is different from the 90 Hz (FIG. 8D) and is observed from the different slopes in time.

FIG. 9 portrays synthetic data velocity analysis by semblance, as discussed in Example A. Note that the best velocity will align the data along constant time and correspond to a maximum semblance value.

FIG. 10 shows measurement of the synthetic data amplitude decay, as discussed in Example A. The decibel (logarithmic) scale linearizes the exponential decay.

FIGS. 11A and B show measured velocity dispersion (FIG. 11A) and amplitude decay (FIG. 11B) of the synthetic data, from Example A.

FIG. 12 shows field data from the Logan, Utah site, from Example A.

FIGS. 13A and B show SH-Wave Data (2-7 m), specifically: measured velocity dispersion from silt interval in Utah data (FIG. 13A) and amplitude decay from silt interval in the Utah data (FIG. 13B) from Example A.

FIGS. 14A and B show SH-Wave Data (8-13 m), specifically: measured velocity dispersion from sand interval in Utah data (FIG. 14A) and amplitude decay from sand interval in Utah data (FIG. 14B) from Example A.

FIG. 15 shows field data from the Boise, Id. site, from Example A.

FIGS. 16A and B show SH-Wave Data (5-10 m), specifically: measured velocity dispersion from upper interval (5-10 m) in Idaho data (FIG. 16A), and amplitude decay from upper interval in Idaho date (FIG. 16B), from Example A.

FIGS. 17A and B show Idaho SH-Wave Data (10-15 m), specifically, measured velocity dispersion (FIG. 16A) from deeper interval (10-15 m) in Idaho data, and amplitude decay (FIG. 16B) from the deeper interval (10 to 15 m) in Idaho date, from Example A.

FIGS. 18A and B portray Kelvin-Voigt (KV) soil representation for (FIG. 18A) vibrator and for (FIG. 18B) wave assemblage, as discussed in Example B.

FIGS. 19A and B portray Kelvin-Voigt-Maxwell-Biot soil representation for (FIG. 19A) vibrator and (FIG. 19B) wave assemblage, as discussed in Example B.

FIGS. 20A and B portray Equivalent KV (FIG. 20A) damping and (FIG. 2-B) stiffness for a KVMB thought experiment, as discussed in Example B.

FIG. 21 shows Equivalent KV damping ratio as a function of KVMB damping ratio for different mass ratios, as discussed in Example B.

FIG. 22 illustrates a method for determining a lumped spring stiffness from a soil element's shear modulus, $G_f$, as in Example B.

FIG. 23 is a plot of Equivalent KV damping ratio as a function of hydraulic conductivity at 50 Hz for different porosities, as discussed in Example B.

FIG. 24 A-C portray frame and water time histories corresponding to points A, B, and C of FIG. 23, in Example B.

FIG. 25 is a plot of Equivalent KV damping ratio as a function of natural frequency for a porosity of 30% for different hydraulic conductivities corresponding to points A, B, and C of FIG. 23.

DETAILED DESCRIPTION OF THE PREFERRED EMBODIMENTS

Referring to the figures, there are shown several, but not the only, embodiments of the invented system, which may include methods, apparatus, and/or programming code means for determination of permeability from damping.

Figure 1:
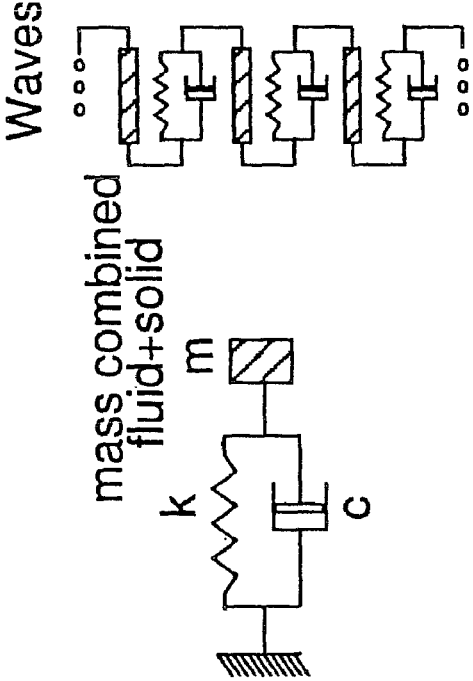
FIG. 1 is a schematic portrayal of prior art KV (Kelvin-Voigt) representations, next to an embodiment of the invented KVMB representations.

Referring to FIG. 1, there is schematically shown a KV representation (on the left) and an embodiment of the invented KVMB representation (on the right), which splits the mass component into both fluid and solid parts (using porosity). A key component of the preferred embodiments of the invention is the diagonalization of the representations, and then selecting the two complex conjugate eigenvalues of the KVMB system to compute an equivalent KV damping ratio. The eigenvalues depend on the KVMB dashpot, which the preferred embodiments relate to permeability. Thus, using embodiments of the invention, any existing method that employs the KV representation may now be related to the KVMB representation, and, hence, to permeability of the fluid through the solid.

Required Givens

Preferred embodiments of the procedure begin with the following properties that must be given.

Porosity n: The material's porosity must be known (unitless). This may be obtained either by conventional logging methods for borehole surveys, or by standard laboratory methods, for example.

KV Damping Ratio $\delta_{kv}$: If the source of this damping ratio value is a vibration test, damping ratio will be specific to the frequency and sample dimensions of the test. In terms of lumped properties (spring stiffness k, dashpot c, total mass m):

$$\delta_{kv} = \frac{c}{2\sqrt{k \cdot m}} \qquad (1)$$

If the source of this damping ratio value is a shear-wave survey, then viscoelastic damping ratio will be frequency-dependent, and must be computed for an angular frequency determined by a chosen analysis length L. The angular frequency is given by:

$$\omega = \frac{\sqrt{C_1}}{L} \qquad (2)$$

Damping ratio will then be given as:

$$\delta_{kv} = \frac{\omega \cdot C_2}{2 \cdot C_1} \qquad (3)$$

where stiffness C1, and damping C2, are the constant coefficients of the 1-D viscoelastic wave equation:

$$\frac{\partial^2 u}{\partial t^2} = C_1 \frac{\partial^2 u}{\partial x^2} + C_2 \frac{\partial^3 u}{\partial t \partial x^2} \qquad (4)$$

where u is particle displacement, x is the spatial coordinate of wave propagation, and/is time. A field method for obtaining C1 (units $m^2/s^2$) and C2 (units $m^2/s$) is given in Example A below.

Specific Gravity of the Solids $G_s$: This is unitless and determined by standard laboratory methods. The preferred embodiments of the invention are not very sensitive to this value. A value in the range of 2.6 to 2.7 should work quite well for most geologic materials.

Mass Density of the Saturating Fluid $\rho_f$: Typically, the saturating fluid will be water, but could be oil or some other fluid. Therefore, mass density may be determined from known data and/or known methods.

Preferred Procedures

1. Compute Lumped Masses: Assuming saturated conditions, compute the lumped component masses for the solid, $M_s$, and the fluid, $M_f$. One can assume any cross-sectional area A for these values (typically one would use unity m$^2$), but the length of the sample or the analysis length L is important, and must agree with the frequency chosen for the mapping. See equations (5) and (6), below:

$$M_s = (1-n) G_s \rho_f A \cdot L \quad (5)$$

and $$M_f = n \rho_f A \cdot L \quad (6)$$

Figure 2:
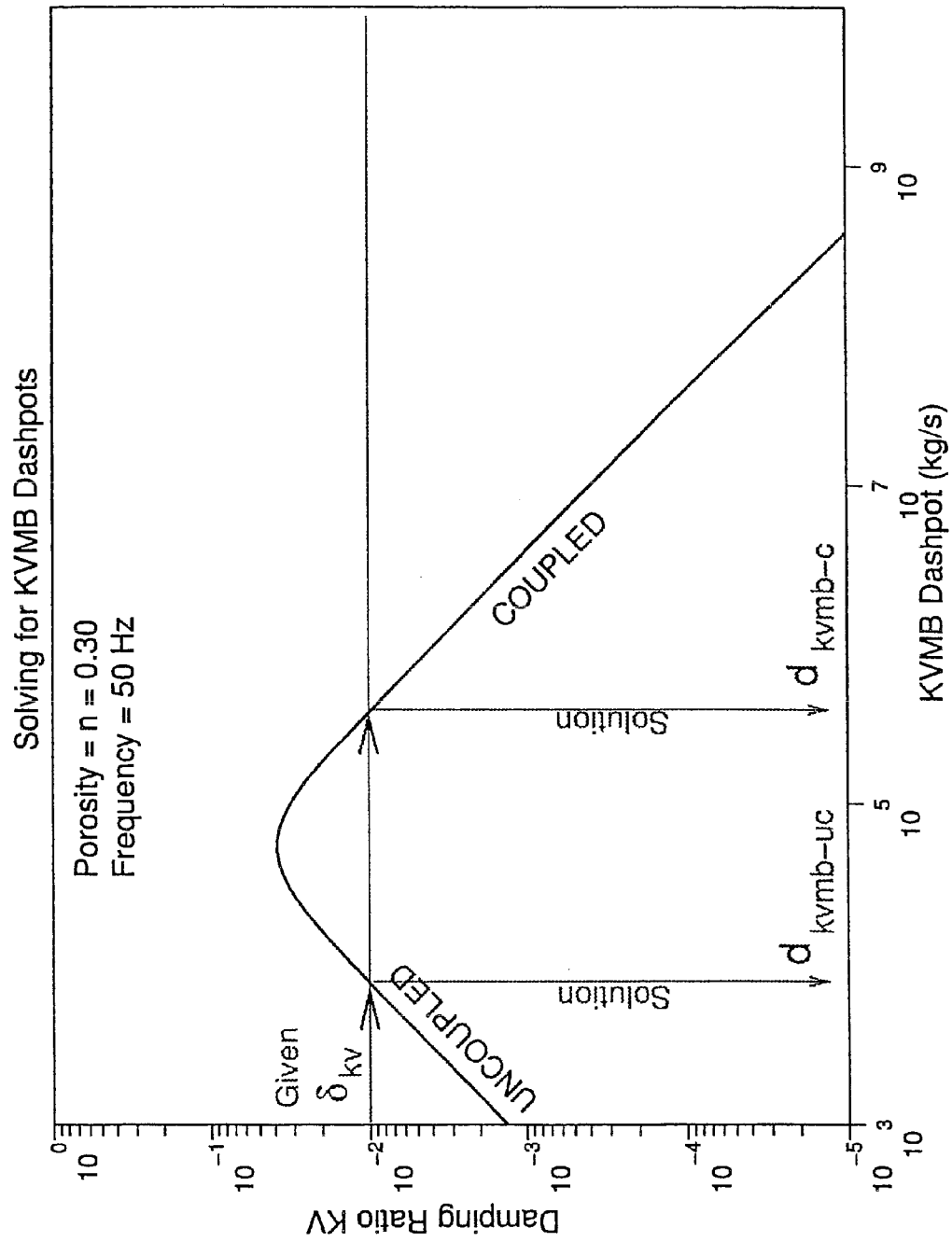
FIG. 2 is a map, according to one but not the only embodiment of the invention, of damping ratio plotted vs. KVMB dashpot, illustrating solving for KVMB dashpots given KV damping ratio. Note the two possible solutions, kvmb-uc (uncoupled) and kvmb-c (coupled) of which the coupled solution is typically the best choice.
Figure 3:
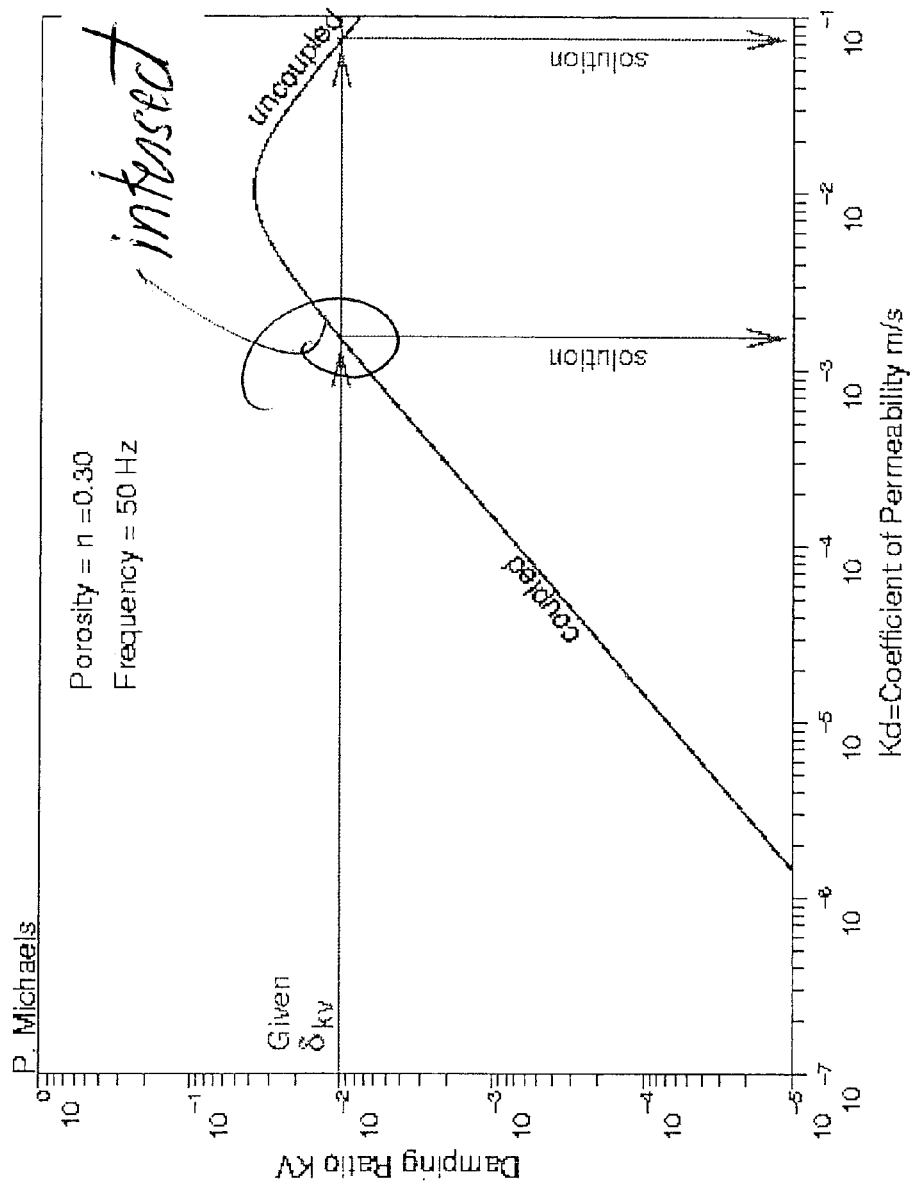
FIG. 3 is a "KV to KVMB map," according to one but not the only embodiment of the invention, comprising, wherein damping ratio is plotted vs. coefficient of permeability. Note, again, the two solutions.

2. Mapping from KV Damping Ratio to KVMB Dashpot: Given the above masses, $M_s$ and $M_f$, porosity n, and the solid frame lumped spring stiffness k, there exists a curve that maps the Kelvin-Voigt damping ratio ($\delta_{kv}$) to the KVMB dashpots ($d_{kvmb}$) as described in Example B, below. This mapping is of key importance to preferred embodiments of the invention, and, the inventor believes, is not obvious to those of average skill in the art. Said mapping comprises diagonalization of the 2×2 KV oscillator and the 3×3 KVMB oscillator systems, then relating the two complex conjugate eigenvalues of the KVMB system to the eigenvalues of the KV system. The curve is concave downward, exhibits a peak that separates the largely coupled from the largely uncoupled conditions. The KVMB dashpot will span many orders of magnitude, and is directly related to the material permeability $K_d$ (units of m/s). The greater the permeability, the smaller the dashpot. See examples in FIGS. 2 and 3.

3. Compute the Two KVMB Damping Ratio Solutions: There will be a largely coupled and a largely uncoupled solution to the mapping problem (see FIG. 2). Solutions are located at the intersection between a line of constant damping ratio, $\delta_{kv}$, and the concave downward curve that maps the $\delta_{kv}$ damping ratio to the $d_{KVMB}$ dashpots. The line of constant KV damping ratio is given by the field or laboratory experiment, and must fall below the peak of the KV-KVMB curve (otherwise, there is no solution).

Best Solution by an Iterative Method: A) One computes brackets for the coupled and uncoupled searches. The brackets are joined at the peak of the curve shown in FIG. 2. The maximum dashpot bracket is set by computing a dashpot that corresponds to a minimum expected permeability (see equation 7, below). The minimum dashpot bracket is set by computing a dashpot that corresponds to a maximum expected permeability. B) One performs bisection searches in each bracket seeking a solution by invoking a function that computes a KV damping ratio from a trial KVMB dashpot. Sensible changes to the KVMB dashpot are made until the computed KV damping ratio matches (within some tolerance) the given KV damping ratio obtained from a field or laboratory experiment.

4. Compute Permeability Values Corresponding to the KVMB Dashpots: For each KVMB dashpot, the corresponding permeability value will be given by:

$$K_d = \frac{n^2 g \rho_f A \cdot L}{d_{kvmb}} \quad (7)$$

The best solution will be the coupled solution for most geologic materials. The reasons for this are as follows. First, it would require a very large permeability to fall in the uncoupled region. Most earth materials do not present this large a permeability. Second, the result is largely insensitive to frequency for the coupled case. That is, consistent solutions are obtained for a wide range of sample lengths or resonant frequencies. If a material has large permeability (for example, very course gravel), then one must choose a frequency for the mapping that is equal to the frequency at which the measurement of $\delta_{kv}$ was made.

Referring to Example C, there is shown one embodiment of software/programming that may be used in embodiments of the invention. The programming computes a determination of permeability from KV shear-wave-based measurements of stiffness, damping, and neutron logged porosity. Specifically, this KD-4X.sci program embodiment incorporates the inventor's methods such as described elsewhere in this disclosure, for inversion of stiffness and damping (KV) to KVMB dashpot and permeability.

Embodiments of the invention may comprise using apparatus and/or methods that are currently known in the literature and/or available commercially. Cross-well, down-hole, resonant column, down-hole vibrators, surfaces sources, geophone arrays, and/or VSP may be used, for example. Visual Sample Plan (VSP) methods are available from Pacific Northwest National Laboratory, for example, at http://dqo.pnl.gov/vsp/vspdesc.htm; VSP methods have been described as "a simple, defensible tools for defining an optimal, technically defensible sampling scheme for characterization. VSP is applicable for any two-dimensional sampling plan including surface soil, building surfaces, water bodies, or other similar applications." FIG. 4 schematically portrays some, but not the only, radiation patterns and conditions for equipment that may be used in physical testing to obtain data in some embodiments of the invention.

Examples of methods and equipment that might be used to provide data for analysis in procedures according to the preferred embodiments are disclosed by Paulsson Geophysical Services, Inc.'s "Long Bore-hole Array." For example, currently-available commercial equipment may be used, such as a down-hole vibrator (10-1400 hz, 20,0000 ft max depth) and 3-component receiver arrays (to deploy 80-400 levels of three component geophones, no practical bandwidth limitations, clamping via fluid inflatable bladders, deployed by production tubing or drill pipe). See FIG. 4, for example. For background on bore-hole equipment, see Paulsson U.S. Pat. Nos. 4,751,688, 4,783,771, and 4,805,725. Equipment or services from other companies that test or log oil wells may be used in combination with the data handling and analysis of this disclosure.

Example A

In-Situ Determination of Soil Stiffness and Damping—Methods and Apparatus

Determination of in-situ dynamic soil properties is fundamental to the prediction of the seismic behavior of foundations and soil embankment structures. Both elastic (stiffness) and inelastic (damping) values are required for computational analysis. To be of value to engineers, the geophysical inversion should employ the same soil model as used in the dynamic analysis software. Current engineering practice employs a Kelvin Voigt (KV) model (spring in parallel with dashpot). The relevant wave equation is a third order partial differential equation. This Example A demonstrates how to collect in-situ field data and solve for stiffness (scaled shear) and damping values by a method consistent with this constitutive model. Measurements of the seismic wave's amplitude decay and velocity dispersion are simultaneously inverted for the required stiffness and damping values. These in-situ determined stiffness and damping values are directly comparable to those obtained by resonant column measurements in the laboratory. Furthermore, the results may be directly input into currently available engineering software to provide values of stiffness and viscous damping. This paper includes both synthetic (finite difference) and field data examples which illustrate the method.

In the interest of clarity, steps common to all in-situ determinations of dynamic soil properties are identified, as follows:
1. The recording of in-situ wave propagation data.
2. Taking measurements from the recorded waveform data.
3. Calculation of dynamic soil properties from the measurements.
4. Mapping errors in observed measurements to errors in calculated soil properties.

The first step is accomplished by field experiments such as down hole, cross hole, or surface seismic recording. In the second step, measurements are taken from the recorded field data. For example, in elastic analysis, the measured quantities might be travel times and distances. Note that these measurements are not the dynamic properties of interest. Dynamic properties are calculated, not measured. Calculation of dynamic soil properties is done in the third step. The calculation is done under a constitutive model and corresponding governing differential equation. In fact, the concept of each dynamic property is intimately bound with the assumed constitutive model. There is no concept of a soil damping value under an elastic constitutive model. Thus, when SH wave velocity is accounted for under an elastic model, there is only one soil property, the stiffness of the soil. If damping is actually present, some portion of the velocity will incorrectly be attributed to stiffness. Thus, the computation of a shear modulus from wave velocity will be in error if significant viscous damping is present.

It is interesting to note that the same set of recorded waveform data (collected by whatever means) may be subjected to different measurement and calculation procedures, depending on the model assumed. Changing either the constitutive model or the measurements taken from the data will lead to different determinations of soil properties for the same field experiment. The different types of field experiments only fix the relevant boundary conditions and wavefield sampling.

The specific calculations in steps 3 and 4, above, are done under a mathematical formalism known as inverse theory. Inverse theory is well documented. A good text on the subject is Menke (1989). Further examples of inverse theory may be found in Lines and Levin (1988).

Review of In-Situ Methods

Various researchers have conducted in-situ determination of rock and soil dynamic properties, using a variety of experimental protocols over the last tree decades. An example of the least invasive method is a surface wave experiment conducted with both source and receivers on the surface of the earth. Rayleigh waves (a combination of both compressional and shear waves) have proved particularly useful in this regard (Nazarian and Stokoe, 1984). The inverse method, Spectral Analysis of Surface Waves (SASW), is typically used to determine the shear wave velocity in a horizontally layered earth under an elastic constitutive model. Measurements taken from the surface waves yield velocity dispersion as a function of frequency. The dispersion curves are then inverted to determine actual soil velocities. Under an elastic model, this dispersion is entirely due to the soil layering (configurational dispersion). It would be very challenging to adapt the methods contained in this paper to surface waves. With a KelvinVoigt model, the challenge would be to separate the observed dispersion into two components, configurational and inelastic. Some attempts at surface measurement of attenuation have been tried using a different wave type. Stoll (1983) documents the use of refracted acoustic waves in a marine environment to solve for a complex modulus.

In sandy or fine grained soils, the Seismic Cone Penetration Test (SCPT) can be used without actually drilling a borehole (Robertson et al., 1985). In this test, a standard cone penetrometer is modified to include a horizontally oriented geophone. The modified penetrometer is driven into the soil in the usual fashion for CPT data. Periodically, the penetrometer is halted at different depths and a surface source is excited. Thus, shear waves are recorded along a vertical propagation path. Usually, this path is perpendicular to any horizontally layered boundaries. While the majority of SCPT calculated soil properties have been done under elastic assumptions, there should be no impediment to using SCPT data with the inversion method presented in this Example A.

One practical limitation of the SCPT method is that soils with gravel or cobbles can refuse the penetrometer. Thus, a down hole method is usually preferred when these coarse grained soils are present. An example of the down hole method in gravelly soils may be found in Kokusho et al. (1995). Kokusho found that SH wave velocity did not necessarily depend on void ratio according to traditional expectations for sandy soils. Rather, he found SH wave velocity to be highly dependent on gradation. The finding that gravelly soils are anomalous should be kept in mind when reading the final field example contained here.

The most expensive method used to determine in-situ dynamic soil properties is the cross borehole experiment. The expense is a result of requiring three or more boreholes to be drilled. Typically a source is lowered in one borehole and receivers record horizontally propagating shear waves in the other two boreholes. The reader is referred to standard ASTM D 4428 for a description of the method and the elastic velocity analysis that is typically done. One common application of the crosshole method has been to evaluate in-situ dynamic compaction programs (Diese et al., 1994).

The cross hole method was recently used to great advantage by Salgado et al. (1997). They demonstrated that large strain measurements can be made with this configuration (if one of the receiver boreholes is close enough to the source hole). This is an extremely useful result, since it is the first in-situ method to actually determine the strain amplitude dependence of the shear modulus.

One might hope to apply the inversion method of this paper to cross borehole data. However, since soil layering is typically horizontal, one might expect that any configurational dispersion (wave guide effect) would be difficult to separate from inelastic dispersion due to viscous effects. This is not to say that down hole methods are free from any complications. It is true that scattering effects across layer boundaries will interfere with the down hole measurement of attenuation. However, in the down hole configuration, more sampling within a layer is often possible. This permits better statistical averaging within a layer than is generally possible with only two receiver positions in the cross hole method. From a methodology point of view, the choice between cross hole and down hole is often one of dealing with complications in measuring dispersion versus attenuation, respectively. With regards to total cost, down hole is generally less expensive.

Down-Hole Experiment

The present inventor's field data were acquired using a moveable down hole three-component clamped geophone and a stationary three-component reference phone. The reference phone is used to compensate for small variations in source strength, spectral content, and any possible trigger variations. FIG. 5 shows the author's typical arrangement of a down hole experiment. The borehole and reference phone are usually about one meter from the source. This provides a nearly vertical propagation path for the waves in all but the shallowest levels. The reference phone is buried about 10 cm to protect it from noise sources at the surface. Multiple source efforts are acquired and summed at each borehole station. Typically five efforts will significantly overcome random background noise. Borehole geophone stations are acquired at regular intervals, 0.5 or 0.25 meter, depending on the detail desired.

FIGS. 6A and B show two SH wave sources built by the present inventor. FIG. 6A shows a horizontal hammer blow source with hold-down weight, and FIG. 6B shows an inclined hammer source (135 degrees from vertical) nailed to soil.

In FIG. 6A, the source is constructed from a 1 meter length of railroad tie. Sledge hammers are pivoted by angle iron supports, and are activated by ropes. Only one hammer is used at a time, with the other hammer being tied off from the beam. The wood beam is struck directly by the broadside edge of the hammer. The soft hammer blows are highly repeatable and produce a useful bandwidth from about 15 to 150 Hz. Sand bags may be placed on the railroad tie to provide a static load which couples the beam to the soil. Coupling is further enhanced by angle iron cleats mounted on the base of the beam. The angle iron pivots and rope activation system protect the operator from back injury that might result from free swings of the hammers. Each geophone level is acquired with two source polarizations so that SH waves may be confirmed and enhanced by a subtraction process.

The other design, as shown in FIG. 6B, is lighter weight and requires no static hold down load other than the weight of the mechanism itself (about 45 pounds). It is nailed to the soil and employs the same soil key lock on the base of the timber. Further, the blows are delivered at 45 degrees from the horizontal, producing a dynamic hold down force. The single hammer pivot point can be rotated to either side, eliminating the need for two hammers. Horizontal data acquired with both sources are quite similar, but the source in FIG. 6B has the added advantage of an extra amount of vertical motion which can be used in P wave studies.

The data of interest are acquired on the horizontal component phones. A Bison 9048 series engineering seismograph was used to collect the data. Because the tool may rotate and change orientation as it moves up the hole, the two horizontal borehole signals must be rotated to a standard phone orientation following hodogram analysis of the particle motion. A hodogram is a 2 dimensional plot of the ground motion time history in the horizontal plane. Based on the measured azimuth of the linear particle motion, a coordinate rotation is performed to project the entire particle motion onto a single horizontal channel. It is the mathematical equivalent of rotating the tool so that one of the phones is aligned parallel to the source polarization.

Choosing a Constitutive Model

Over the years, the calculation of the actual dynamic soil properties has been done under differing constitutive models (Elastic, Kelvin/Voigt and Maxwell being the most common). Kudo and Shima (1970) provide a concise review of some of the early efforts. As they point out, the lack of a definitive consensus on the appropriate constitutive model has been due in large part to the limited bandwidth of the observations. Under conditions of limited bandwidth, almost any model will produce acceptable results.

On the other hand, engineering practice has tended toward the use of the Kelvin Voigt model for consolidation and soil dynamics. Computational examples include SHAKE (Schnabel et al., 1972) and DESRA2 (Lee and Finn, 1982). Furthermore, laboratory measurements by resonant column techniques also invoke the Kelvin Voigt soil model (Hardin, 1965). The laboratory measurements may be done at comparable frequencies, strain magnitudes, and stress conditions to those in a down hole experiment. Further, the determinations of soil properties is often done under the same Kelvin Voigt model. Thus, it is easy to compare laboratory results with the in-situ measurements described in this paper. This is true regardless of the type of boundary conditions invoked for the passive end of the oscillator (fixed or free). The reader of this document is referred to Drnevich et al. (1978) and standard ASTM D. 4015-92.

The major motivation for this work was to refine the acquisition and processing velocity). Measurement of amplitude decay or bandwidth in a resonant column oscillator under this model yields stiffness and damping values which may be directly related to those which will be determined in this paper.

When considering the multiple degree freedom chain of spring mass dashpot elements (assuming for the moment all elements are identical), the finite difference equation of motion is found by summing the stiffness and damping forces. Thus, for the jth element in the chain, $$\frac{\partial v_j}{\partial t} = \frac{\partial^2 u_j}{\partial t^2} \simeq \left(\frac{\Delta x^2 k}{m}\right)\frac{\Delta^2 u_j}{\Delta x^2} + \left(\frac{\Delta x^2 d}{m}\right)\frac{\Delta^2 v_j}{\Delta x^2} \quad (A1)$$

where $u_j$ and $v_j$ are the particle displacement and particle velocity for the jth mass, measured in meters. The spring constant is k and the dashpot damping is d. The element spacing is $\Delta x$. This equation is often cast in matrix form, as was done in generating synthetic data to test the inverse method presented in this Example A.

In the limit of a continuum, difference equation (A1) becomes, $$\frac{\partial^2 u}{\partial t^2} = C_1 \frac{\partial^2 u}{\partial x^2} + C_2 \frac{\partial^3 u}{\partial t \partial x^2} \quad (A2)$$

where u is particle displacement, x is the spatial coordinate, and t is time. The constant, $C_1$, is the stiffness coefficient (spring), and $C_2$ is the viscous damping coefficient (dashpot). The ratio of $C_2$ (m$^2$/s) to $C_1$ (m$^2$/s$^2$) is the relaxation time in seconds.

Biot (1941), in referring to Terzaghi's earlier work, recalled useful analogy for the Kelvin Voigt solid. In effect, the situation is similar to squeezing a permeable sponge underwater. The relaxation time is a measure of how long the sponge takes to resume its initial equilibrium. This depends on the combination of the stiffness of the fibers (spring) and the permeability permitting the fluid to return into the previously squeezed pores (viscous damping).

For a continuum, the coefficients $C_1$ and $C_2$ are given in terms of shear modulus (G), mass density ($\rho$), and absolute viscosity ($\eta$) of the soil model. Therefore, the mapping between the difference equation coefficients and those of the governing differential equation are $$\left(\frac{\Delta x^2 k}{m}\right) \to \left(\frac{G}{\rho}\right) = C_1 \quad (A3)$$

$$\left(\frac{\Delta x^2 d}{m}\right) \to \left(\frac{\eta}{\rho}\right) = C_2 \quad (A4)$$

Modeling soils with greater detail is possible. For example, Biot (1962) and Gajo (1995) characterized the soil as a two-phase medium, keeping fluid and frame motions distinct. Gajo computed the theoretical effects of damping on transient waveforms. However, separate recording of frame and fluid motion is beyond this writer's capability, and the introduction of greater detail results in an increase in the number of unknowns, which often leads to non-uniqueness in the solution to the inverse problem. For these reasons, this writer has chosen to reduce the problem to only two unknowns, stiffness and damping, which admittedly are functionally dependent on other parameters such as fluid viscosity, frame porosity, permeability, and the densities of the fluid and grains.

$$\frac{\partial^2 u}{\partial t^2} = C_1 \frac{\partial^2 u}{\partial x^2} \tag{A5}$$

Ideally, both $C_1$ and $C_2$ are constants independent of frequency. Furthermore, both $C_1$ and $C_2$ should be properties of the medium. In reality, other factors also are relevant to the establishment of effective values for these two "constants." For example, in the elastic limit, $C_1$ is the square of the phase velocity of the wave. The phase velocity depends on the shear modulus, which in turn has been shown empirically to depend on a number of parameters which include the magnitude of the strain, the stress field, and the void ratio of the material (Hardin and Richart 1963).

It is difficult to underestimate the appeal of the Kelvin-Voigt (viscous damping) model. While it is clear that water saturated soils should exhibit a viscous interaction with the frame, it is far less obvious that a dry soil should exhibit viscous behavior. (Grain to grain contact friction is the more likely dominant cause of energy dissipation.) Therefore, Hardin (1965) found it necessary to vary viscosity as a function of frequency for dry specimens. In short, he suggested that the product of viscosity with frequency divided by shear modulus should be held constant. Hardin's suggestion has the effect of eliminating velocity dispersion, linearizes the variation of decay, $\alpha$, with frequency, and establishes a constant Q (quality factor) medium. The writer has decided not to vary $C_2$ in a similar fashion, because doing so would suggest that a different constitutive relationship might be more appropriate. One alternative for dry soils might be a micromechanical approach invoking a contact law (Cascante and Santamarina 1996). Attempts to apply the writer's procedure within the vadose zone have not supported the Kelvin-Voigt model. (Holding $C_2$ constant in dry soils does not seem appropriate.) For that reason, the only field examples presented here are taken from below the water table.

Application to a Soil Profile

The practical matter of dividing the subsurface into layers involves three considerations:
1. Each layer thickness must be great enough for dispersion and attenuation to be measured with some confidence. Multiple sample points within a layer are needed to determine error bars.
2. Each layer should not be so thick that a significant variation of stress occurs across the layer. This problem is greatest in the first few meters below the surface.
3. The layer boundaries should avoid combining significantly different soil types in the same layer, subject to the resolution limits imposed by the available source band width (see next section).

In the writer's experience a nominal layer thickness of about 5 m with 0.5 to 0.25 intervals between geophone stations seems to satisfy the above requirements for layers in the 5 to 25 m depth range.

Limits on Resolution

The ultimate limits on spatial resolution depend on the bandwidth and frequencies present in the source radiation. This is true for all seismic methods—down-hole, cross-hole, or conducted on the surface. In the context of typical soil velocities, and the writer's hammer sources, the available wavelengths will range from 50 m to 1 m. Although increasing the high-frequency content might appear desirable in the context of resolution, it must be cautioned that the relaxation mechanism will change as the pore fluids begin to move with the frame. This change begins at about 100 Hz for many soils.

The third principle in the preceding section suggests that the relevant elementary volume should avoid inclusion of different soil types. This is only true if the distinct soil types occur in layers which are thick in the context of the dominant wavelengths radiated by the source. Even relatively extreme variations in soil types may be combined into a single relevant elementary volume, if they are thin as measured by the available seismic wavelengths (i.e., below the resolution of the source radiation).

Forward Problem

For any given values of $C_1$ and $C_2$ one must be able to calculate the frequency dependent attenuation and body wave dispersion. The needed formulas may be derived by substituting the trial solution, $$u(x,t) = \exp(-\alpha x) \cdot \cos(\beta x - \omega t) \tag{A6}$$

into (A2). The complex part of wavenumber, $\alpha$, is an attenuation coefficient (measured in 1/meters), a function of frequency. The real part of wavenumber is $\beta$, and $\omega$ is frequency. The result is $$[2C_1\alpha\beta - C_2(-\alpha^2\omega + \omega\beta^2)]\sin(\beta x - \omega t) + [C_1(\alpha^2 - \beta^2) - 2C_2\alpha\omega\beta + \omega^2]\cos(\beta x - \omega t) = 0 \tag{A7}$$

Because (A7) must be true for all time values, t, and space values, x, the coefficients of the sine and cosine terms must equal zero. This results in two equations in two unknowns:

$$\begin{bmatrix} (2\dot{\alpha}\hat{\alpha}) - (-\hat{\alpha}^2\dot{u} + \dot{u}\hat{\alpha}^2) \\ (\hat{\alpha}^2 - \hat{\alpha}^2) - (2\dot{\alpha}\dot{u}\hat{\alpha}) \end{bmatrix} \cdot \begin{bmatrix} C_1 \\ C_2 \end{bmatrix} = \begin{bmatrix} 0 \\ -\ddot{u}^2 \end{bmatrix} \tag{A8}$$

Solving equation (A8) for $C_1$ and $C_2$ produces $$C_2 = \frac{2\alpha\beta\omega}{(\beta^2 + \alpha^2)^2} \tag{A9}$$

and $$C_1 = \frac{(\beta^2 - \alpha^2)\omega^2}{(\beta^2 + \alpha^2)^2} \tag{A10}$$

Solving (A9) and (A10) for attenuation ($\alpha$) and phase velocity ($c = \omega/\beta$) leads to the forward equations needed in the design of a least squares inversion algorithm, in which a and c are measured from the down-hole seismic waveforms as a function of frequency.

Let's begin by taking the ratio of (A9) to (A10). Solving the resulting quadratic formula for wavenumber, $\beta$, yields $$\beta = \frac{\alpha}{2C_2\omega} \cdot D \quad \text{(A11)}$$

where $$D = 2\left[C_1 + \sqrt{C_1^2 + \omega^2 C_2^2}\right] \quad \text{(A12)}$$

Substituting (A11) for $\beta$ in (A10) and solving for the attenuation, $\alpha$, produces $$\alpha = \frac{4\sqrt{D}\,\omega^2 C_2}{(2\omega C_2)^2 + D^2} \quad \text{(A13)}$$

Note that if the damping coefficient, $C_2$, vanishes, there is no attenuation. Furthermore, the constant, nonzero value of $C_2$ predicts the frequency dependent behavior of attenuation, $\alpha$.

Replacing wavenumber, $\beta$, with $\omega/c$ and solving for phase velocity, c, one obtains $$c = \frac{2\omega^2 C_2}{D\alpha} \quad \text{(A14)}$$

The frequency dependent behavior of phase velocity depends on both $C_1$ and $C_2$. If damping, $C_2$, vanishes, the phase velocity reduces to the elastic case and becomes a constant (no dispersion). Applying L'Hospital's rule (since $\alpha$ also vanishes), one obtains a constant phase velocity for the zero damping case:

$$c = \sqrt{C_1} \quad \text{(A15)}$$

Eqs. (A13) and (A14) provide the forward equations needed for the inversion algorithm. The section on inversion shows how measurements of both $\alpha$ and c, made at selected frequencies, are then jointly inverted for the constants $C_1$ and $C_2$, stiffness and damping. Before consideration of the inverse problem, however, the mathematical relationships connecting $C_2$ to other common expressions of damping will be described.

Relationship of $C_2$ to Other Forms

While the Kelvin-Voigt model appears frequently in the literature, a number of forms have been chosen to express viscous damping under this model. These forms include complex modulus, loss tangent, loss angle, and damping ratio. For the benefit of those readers who work with these other forms, the following summary is given.

One may define a complex shear modulus of the form $$G^* = G_R + iG_I \quad \text{(A16)}$$

with real part, $G_R$, and complex part, $G_I$. This modulus is related to the wave equation coefficients by $$C_1 = \frac{G_R}{\rho}; \quad C_2 = \frac{G_I}{\omega\rho} \quad \text{(A17a, b)}$$

The complex shear modulus, $G^*$, varies as a function of frequency in the Kelvin-Voigt model. This variation is linear and entirely due to the complex part, $G_I$, and its relation to $C_2$ in (A17).

An alternative form may be computed from the complex shear modulus. This expression is the loss tangent. The loss tangent is given by $$\tan(\delta) = \frac{G_I}{G_R} \quad \text{(A18)}$$

where $\delta$ is the loss angle. It follows from (A17) that $$\tan(\delta) = \omega\left(\frac{C_2}{C_1}\right) = \omega T_r \quad \text{(A19)}$$

Here, $T_r$ is the relaxation time. Loss tangent (or loss angle) will also vary with frequency. In the Kelvin-Voigt model, the variation is linear with the slope being the relaxation time.

Finally, resonant column workers often employ the concept of damping ratio (Drnevich 1978). Damping ratio, $D_T$ (the ratio between any value of damping to critical damping) is given by $$D_T = \frac{C_2\omega_0\rho}{2G_R} \quad \text{(A20)}$$

where $\omega_0$ is the resonant frequency. The resonant frequency is given by the root of the ratio of the equivalent spring constant to polar moment of inertia in a resonant column experiment (Drnevich et al. 1978).

Inversion of Attenuation and Dispersion

The inverse problem is to solve for wave equation coefficients $C_1$ and $C_2$ (soil stiffness and damping), given measurements of body wave dispersion and attenuation. The joint inversion of two different data types can be linearized and formulated as an iterative matrix inversion scheme using a Taylor's series expansion limited to the first order terms (Menke 1989). The general form is $$G \cdot \Delta m = \Delta d \quad \text{(A21)}$$

The Jacobian matrix, G, contains the derivatives of the measurements (phase velocity and attenuation) with respect to the desired parameters ($C_1$ and $C_2$). The vector, $\Delta m$, contains changes to the soil parameters which reduces the least square error between the observed and predicted measurements. The vector, $\Delta d$, contains the differences between the observed and calculated measurements.

For this specific problem, the matrix equation (A21) is partitioned as follows:

$$\begin{bmatrix} \vdots & \vdots \\ \vdots & \vdots \\ \frac{\partial c}{\partial C_1} & \frac{\partial c}{\partial C_2} \\ \vdots & \vdots \\ \hline \vdots & \vdots \\ \frac{\partial \alpha}{\partial C_1} & \frac{\partial \alpha}{\partial C_2} \\ \vdots & \vdots \\ \vdots & \vdots \end{bmatrix} \cdot \begin{bmatrix} \Delta C_1 \\ \Delta C_2 \end{bmatrix} = \begin{bmatrix} \vdots \\ \Delta c \\ \vdots \\ \hline \vdots \\ \Delta \alpha \\ \vdots \\ \vdots \end{bmatrix} \quad \text{(A22)}$$

The upper partition of G contains the derivatives of phase velocity, c, with respect to the unknown soil parameters. Similarly, the lower partition contains the decay derivatives. Each row of (A22) corresponds to a different sampled frequency. The seismic signals are filtered with narrow bandpass filters to observe the frequency dependent behavior of velocity and decay. Each filtered version of the waveforms contributes two rows to the matrix, one for velocity and the other for decay.

The procedure is iterative, beginning with an initial guess for values of $C_1$ and $C_2$. Solution of (A22) leads to sensible changes in $C_1$ and $C_2$ that reduce the difference between the observed measurements and calculated predictions from equations (A13) and (A14).

In this joint inversion, we have two different types of measurement units in the vector, $\Delta d$. These are velocity (m/s) and decay (1/m) at each sampled frequency. This requires a weighting scheme to properly balance the influence of each type of measurement magnitude on the final answer. Since the numerical magnitude of the data values is dependent on the units, one must weight the attenuation measurements (values in the range of tenths) to achieve parity with the velocity measurements (values in the hundreds).

The writer uses a combination of both row and column weighting when inverting (A22). Rows within a partition are weighted to compensate for the difference in data units. This basic block weighting of the rows may be further modulated by the reciprocal of the standard deviation for each measurement of velocity and attenuation. Thus, the best data (least uncertainty, small standard deviation) are given greater weight in achieving the solution. Estimates of standard deviation (error bars) for each data type are available from the many different geophone locations within a soil layer which redundantly contribute to measurement of velocity and decay.

Column weighting is done to improve the numerical stability of the calculation. The reciprocal of the maximum derivative in each column is used for the column weighting.

The weighted problem is written as follows:

$$[W \cdot G \cdot Y] \cdot Y^{-1} \cdot \Delta m = W \cdot \Delta d \quad (A23)$$

where W is the (n×n) row weighting matrix, and Y is the (2×2) column weighting matrix. The diagonal row weighting matrix (for n frequencies) is given by $$W = \begin{bmatrix} W_{c11} & 0 & 0 & 0 & 0 & 0 \\ 0 & W_{cii} & 0 & 0 & 0 & 0 \\ 0 & 0 & W_{cnn} & 0 & 0 & 0 \\ \hline 0 & 0 & 0 & W_{a11} & 0 & 0 \\ 0 & 0 & 0 & 0 & W_{aii} & 0 \\ 0 & 0 & 0 & 0 & 0 & W_{annf} \end{bmatrix} \quad (A24)$$

where the ith weights for the upper and lower partition are $$w_{cii} = \frac{B \cdot \overline{\alpha} \cdot \sigma_{cmin}}{\overline{c} \cdot \sigma_{ci}} \quad (A25)$$

$$w_{aii} = \frac{(1-B) \cdot \sigma_{amin}}{\sigma_{ai}}$$

Here B is a balance factor which can be used to trim the desired weighting of the relative influence of each data type in achieving a solution to (A23). Equal weighting corresponds to a value of 0.5 for B, the typical choice. The over-lined variables are the respective mean values of the measured attenuation and velocity. The remaining factors are the standard deviation estimates associated with each measurement, normalized by the minimum standard deviation for each type of data.

The diagonal column weighting matrix is given by $$Y = \begin{bmatrix} y_{11} & 0 \\ 0 & y_{22} \end{bmatrix} \quad (A26)$$

where the diagonal elements are equal to the reciprocals of the maximum values found in each column of matrix G respectively.

The least squares solution to (A23) is given by Menke (1989):

$$\Delta m = H \cdot \Delta d. \quad (A27a)$$

$$H = Y \cdot [(WGY)^T \cdot (WGY)]^{-1} \cdot (WGY)^T \cdot W \quad (A27b)$$

Here H is the weighted least squares inverse. Typically, the algorithm converges in about 5 iterations.

Once the algorithm has converged on a solution for soil parameters $C_1$ and $C_2$, one must determine corresponding error bars. What is needed is a mapping between the error bars of the calculated quantities ($C_1$ and $C_2$) and the error bars of the measured quantities (c and $\alpha$) at each frequency. Inverse theory provides a solution to this problem (Menke 1989).

Error bars for the wave equation coefficients (soil stiffness and damping) are the diagonal elements of the matrix, $C_m$, given by $$C_m = H \cdot C_d \cdot H^T \quad (A28)$$

where $C_d$ is the measurement covariance matrix. For uncorrelated measurement errors, $C_d$ is diagonal, and the non-zero elements are the squares of the standard deviations for each measurement. The square of each measurement standard deviation is the estimate of the variance about the measurement value.

Measure of Dispersion and Attenuation

Ideally, the measurement of velocity dispersion should be done by a robust method which also provides an estimate of the uncertainty of each measurement. Methods based on only two receiver positions (such as the cross-spectrum between two signals from different depths) are vulnerable to modulations introduced from reflections and other indirect wave fields. The multisignal summations conducted in a semblance calculation provide an effective frequency-wavenumber filter that excludes non-direct waves. Further, the average property obtained for an interval will include contributions from each sampled position in the interval (rather than relying on only two points). The writer's method is as follows. For a given subsurface interval of interest, different trial velocities are used to adjust the data into alignment. A semblance value (Sheriff 1991) is computed for each trial velocity, and a search performed to find the optimum velocity and corresponding alignment. The semblance value defines an objective function which must be maximized. This is a nonlinear optimization problem. The maximum is found by a golden section subroutine, which is an adaptation to an algorithm found in the work of Press et al. (1989).

Filtering of the data is one way to measure the variation of velocity with frequency. Selection of filter bandwidth requires a compromise between spectral and temporal resolution. The more narrow the bandwidth of the filter, the less will be the temporal resolution, and vice versa. The writer prefers to use an autoregressive, causal band-pass filter with a bandwidth no greater than 2 Hz. The filters introduce phase delays in the data. However, for any given filter, the delay will be the same for all the geophone stations. Thus, the phase delay will have no effect on the measured velocity.

The error bars for velocity at any measured frequency are found by time shifting the data into alignment with the determined velocity. Then, using one signal as a reference, the relative misalignments between the traces are computed by taking the normalized inner product between traces. The more perfect the alignment, the smaller the error bar will be.

The same filters are also used to measure the variation in amplitude decay with frequency. The filtered data are scanned for RMS amplitude of the direct wave as a function of source-receiver distance. The amplitudes are then corrected for spherical divergence spreading loss and a linear fit made on the logarithm of the corrected amplitudes as a function of propagation path length. The slope of the linear fit yields the decay coefficient, $\alpha$. The least square error of the fit is used in the determination of the decay coefficient error bars. The more perfect the fit, the smaller the error bar.

Demonstration on Synthetic Data

A synthetic data set simulating a down-hole experiment was generated by Runge-Kutta integration of the finite difference equation. Eq. (A1), cast in matrix form, was used to calculate the waveforms. The spatial sampling was 0.2 m and the temporal integration interval was 0.0001 s. The simulated source had a peak frequency of 50 Hz and a nominal −6 dB bandwidth of 40 Hz. The synthetic data were resampled to 0.0002 s sample interval after generating the waveforms (comparable to the field recordings to be presented later). The 1-D chain of Kelvin-Voigt elements simulated a 40 m medium. Data corresponding to offsets in the range from 6 to 11 m were then selected for analysis (the selection avoided reflections from the end of the modeled medium). The stiffness and damping were set at $C_1=160,000$ m$^2$/s$^2$ and $C_2=200$ m$^2$/s.

Because a 1-D calculation corresponds to a plane wave, a spherical divergence beam spreading decay was manually applied to the data. This was done by scaling the signal amplitudes by the reciprocal of the distance from the source. This 1/R amplitude scaling simulates a 1/R$^2$ decay in power density associated with a spherical wavefront.

FIG. 8 shows several views of the synthetic data. The true amplitude (after spherical divergence added) is shown in FIG. 8(a). The rapid amplitude decay is quite evident. To better show the changes in the propagating wavelet, FIG. 8(b) presents the data with each signal rescaled by the L2 norm. The L2 norm is simply the Euclidean norm. It is found from the square root of the sum of the squares of the samples in any given signal. The changes in the wavelet due to dispersion are rather modest given the short window of observation (5 m). The wavelet does change with distance since the different frequencies propagate with different velocities (dispersion).

Clear evidence of dispersion can be seen in FIGS. 8(c) and (d). These are the 30 and 90 Hz filtered versions of the synthetic data (2 Hz bandwidth, 14 pole filters). The reader can better observe the different velocity for each frequency by laying a straight edge along a line of consistent phase in FIG. 8(c) and observing the misalignment with the waves in FIG. 8(d), which are faster. The velocity at each frequency corresponds to the slope in time of the wavefront.

An automated method for determining the velocity at each frequency is to apply time shifts to the data for an assumed velocity, and then compute a semblance value to quantify the quality of the trial alignment. FIG. 9 illustrates this trial-and-error procedure of removing travel time with an assumed velocity. This is done for the 30 Hz filtered version. The correct velocity will align the wavefront along a line of constant arrival time. FIG. 9(a) shows that the correct velocity lies between 615 and 363 m/s. The corresponding semblance values are s=0.8169 and s=0.8686 respectively. Perfect alignment with noise free data should result in a value approaching unity. The golden section search procedure determined an optimum estimate of velocity equal to 418 m/s (semblance=0.9413). FIG. 9(b) shows the application of this velocity to align the data. This procedure is performed for each filtered version of the data to measure a dispersion curve.

Determination of the exponential amplitude decay constant, $\alpha$, is done by formulating the problem as a least squares linear regression for each filtered version. At some distance, r, from the source, the Kelvin-Voigt model predicts the wave amplitude, $$A = \left(\frac{A_0 r_0}{r}\right) \cdot e^{-\alpha(r-r_0)} \tag{A29}$$

where $A_0$ is the amplitude of the wave at some reference distance from the source, $r_0$. Multiplying both sides of (A29) by distance, r, and taking the logarithm of both sides leads to an expression for amplitude decay in decibels, $$dB = 20\log_{10}\left(\frac{Ar}{A_0 r_0}\right) = (-20\log_{10}e)\alpha(r-r_0) \tag{A30a}$$

$$dB = (-8.686\alpha) \cdot (r-r_0) \tag{A30b}$$

Thus, the slope of a line on a decibel vs. distance (r−r$_0$) plot is (−8.686)$\alpha$. FIG. 10 shows such a plot for the synthetic data. The decibel (logarithmic) scale linearizes the exponential decay. The value of $\alpha(1/m)$ is easily computed from the slope (dB/m) by dividing by −8.686.

FIG. 12 shows the measurements of decay and dispersion as circles with error bars (95% confidence interval). The calculated dispersion and decay from the solution for $C_1$ and $C_2$ is displayed as a solid curve through the measured points. The solution is quite close to the values of $C_1$ and $C_2$ used to generate the data. The somewhat larger stiffness and damping values result from the additional computational dispersion which is common in finite difference methods. The effect is due to the finite discretization of the computational problem. Mechanical waves propagating through discrete lattice structures also exhibit this type of additional dispersion.

Demonstration on Field Data

Two different borehole surveys have been selected to demonstrate the writer's method. One borehole was located in Logan, Utah, the other in Boise, Id. The Utah data were acquired at the GeoLogan97 field day site. The survey was conducted on Jul. 15, 1997, during the first meeting of the ASCE GeoInstitute. This site exhibits low levels of viscous damping in a soil profile consisting of fine grained sands, silts, and clays.

The Idaho data were acquired in coarse grained granular soils consisting of sands, gravels and cobbles. The Idaho data were collected between episodes of sparging which were being conducted to treat contaminated ground water. The levels of viscous damping are very large at this location.

Utah Case History

FIG. 12 shows the SH-wave data from the horizontal components. Following hodogram analysis for tool orientation, the data were rotated parallel to the source polarization. The signals have been scaled to remove the amplitude decay with depth, permitting the reader to better observe the waveform of the direct arriving wave. Also shown in FIG. 12 is the soil behavior type classification from a neighboring cone penetrometer (CPT-3) survey conducted by ConeTec in November 1996. The CPT survey was done in preparation for the GeoLogan97 meeting.

The change in slope of the first arrivals at the top of the sand clearly indicates a change in wave velocity. The writer chose to apply the method to intervals both above and below this change in velocity. One interval (at 2 to 7 m depth) is in the low velocity saturated silts and clays. The other interval (at 8 to 13 m depth) is in the upper portion of the higher velocity sand. Thus each interval is about 5 m thick and includes about 20 geophone stations (0.25 m station spacing).

The source was the one shown in FIG. 6(b). The entire data set was acquired by the writer without any helper. Working alone, it took 3 hours and 15 minutes to acquire the data. With a helper, this would have been reduced to about 2 hours. The data were collected on a Bison 9048 engineering seismograph with a 0.00025 second sample interval and filters set to 4 and 1,000 Hz.

FIG. 13 shows the dispersions decay for the silt interval. In this and all later presentations, error bars are for 95% confidence limits (random error). Bias will always be present and is difficult to quantify. Bias is introduced by choices, such as the precise limits on the interval, the filter frequencies, and the weighting scheme used in the inversion (all of which affect the resulting $C_1$ and $C_2$ determinations).

Clearly, the lack of velocity dispersion and nearly flat amplitude decay response with frequency suggest a low level of damping. This low level of damping is further supported by the need to reduce the recording instrument preamplifier gain by 20 dB from the normal setting used in Idaho, where signal losses have been greater. The smooth curves in FIG. 13 are the dispersion and amplitude decay computed from the solution:

$$C_1 = 25{,}567 \pm 218 \text{ m}^2/\text{s}^2 \text{ stiffness}$$

$$C_2 = 1 \pm 1 \text{ m}^2/\text{s damping}$$

The relaxation time for the silt (from the ratio of $C_2/C_1$) is only 39±29 µs. Such a short relaxation time, uncertain as it may be, could be an indication that the pore fluids are moving with the frame in this frequency band (presumably due to the low level of permeability that one would associate with finer grained materials). If the fluids are moving with the frame, rather than through it, there would be less viscous drag.

FIG. 14 shows the dispersion and decay measurements for the sand interval (at 8 to 13 m depth). The velocity dispersion is slightly greater than in the silt. The variation of amplitude decay with frequency is significantly greater than for the silt. Again, the smooth curves are computed from the solution:

$$C_1 = 51{,}343 \pm 375 \text{ m}^2/\text{s}^2 \text{ stiffness}$$

$$C_2 = 14 \pm 1 \text{ m}^2/\text{s damping}$$

Damping has increased by a factor of 14, and the stiffness has doubled. For the sand, the relaxation time is computed to be 273±19 µs. Clearly, the role of viscous damping has overwhelmed the increase in stiffness. It may be that the presumed increase in permeability which one would likely associate with a larger effective grain size is partly responsible for the increased damping. That is, the sandy soil may be of sufficient permeability to afford more fluid-frame interaction. The result would be more viscous damping in the sand than in the silt.

Idaho Case History

FIG. 15 shows the Idaho SH-wave data rotated into alignment with the source polarization. Also shown is a description of the material observed during the drilling process. The sudden change in slope of the direct arriving wavefront occurs at the water table, suggesting that the SH-wave speed increases below the vadose zone.

The data were acquired with the horizontal impact source shown in FIG. 6(a). Data collection was on Dec. 20, 1994. Downhole stations were acquired every 0.5 m. The recording instrument was a Bison 9048 engineering Seismograph with a sample interval of 0.0002 s and filters set at 8 and 1,000 Hz. With one helper, the survey took 1 hour and 40 minutes for data collection.

Stiffness and damping for two intervals are presented here. A shallow interval (just below the water table, at 5 to 10 m) was found to exhibit extreme damping. The other deeper interval (at 10 to 15 m) was found to have significantly less damping. Since the wave velocity at the dominant frequency of about 50 Hz is not much different in the two zones, an elastic analysis would fail to detect a significant difference between the two intervals. As will be shown, the difference becomes evident only when one examines velocity and amplitude decay as a function of frequency.

FIG. 16 shows the measured velocity dispersion and attenuation for the upper interval. The smooth curve is calculated from the inversion solution:

$$C_1 = 94{,}917 \pm 2{,}913 \text{ m}^2/\text{s}^2 \text{ stiffness}$$

$$C_2 = 255 \pm 9 \text{ m}^2/\text{s damping}$$

The corresponding relaxation time is 2,686±125 microseconds. It is evident that extremely large viscous forces are causing the dispersion and amplitude decay. The use of a Kelvin model is well justified since the dispersion and decay observed agree well with the model (see Eqs. [A12], [A13], and [A14]). In the language of inverse theory, the error bars in the solution are chiefly a result of errors in the measured quantities (data error) rather than due to the choice of an inappropriate model (resolving error).

One possible contributing factor to the large damping may be residual trapped air in the pores. The survey was conducted four and a half months following the termination of a seven month sparging-ground-water treatment program. At this point, there is no way to know if trapped air was present during the survey. Trapped air would reduce the degree of water saturation. Significant alteration of SH-wave velocity has been documented in partially saturated soils (Wu 1984). In any case, the granular nature of the soils would predict sufficient permeability for interaction between fluids and the soil frame, the result being viscous damping.

FIG. 17 shows the measurements of dispersion and decay for the deeper interval. It is clear that significantly less viscous damping is present from these data. The smooth curves were calculated from the solution:

$$C_1 = 182{,}751 \pm 4{,}860 \text{ m}^2/\text{s}^2 \text{ stiffness}$$

$$C_2 = 69 \pm 17 \text{ m}^2/\text{s damping}$$

The relaxation time for this interval is computed to be 378±94 µs. In comparing the two intervals, it is clear that the lower interval is stiffer with less damping. The fact that damping can raise the velocity of the wave is easily overlooked if not measured. This may be important when computing other quantities such as shear modulus from velocity alone.

Conclusions

Example A

A method for determining in-situ stiffness and damping has been presented. The method is to jointly invert both measurements of SH-wave velocity dispersion and spatial amplitude decay, corrected for beam divergence. The method is consistent with current engineering practice and uses a Kelvin/Voigt constitutive model. The field examples presented here demonstrate that the method works in practice. Furthermore, the current use of the Kelvin-Voigt model in engineering (where pore water is present) is supported by these in situ determinations.

Since damping will increase the wave velocity, it is possible to introduce significant errors by computing shear modulus from wave velocity alone. It has been common practice to compute the shear modulus from measurements of the dominant group velocity of SH-waves. This is like measuring only the resonant frequency in a spring/mass/dashpot experiment, and then computing the spring constant without consideration of any damping effects.

The actual measurement of amplitude decay is essential if damping is to be determined. To measure amplitude decay, the writer's method invokes a significant amount of redundancy and averaging to overcome variations in borehole to formation coupling. This strategy also helps reduce the effects of constructive and destructive interference presented from scattered and reflected waves. Further, it is this redundancy which also permits an estimate of the errors involved.

Finally, the writer would like to speculate that his often observed increase in shear wave velocity at the water table may be an indication of a shift in dominance from contact (grain-grain) friction in the vadose zone to viscous (fluid-frame) friction below the water table. It is likely that both relaxation mechanisms exist at all times, but the high viscosity of water (relative to air) may shift the balance to a viscoelastic model below the water table. Evidence for this conjecture may also be found in resonant column studies of saturated and dry soils (Stoll 1985).

Example B

Relating Damping to Soil Permeability

Published comparisons of complex moduli in dry and saturated soils have shown that viscous behavior is only evident when a sufficiently massive viscous fluid (like water) is present. That is, the loss tangent is frequency dependent for water saturated specimens, but nearly frequency independent for dry samples. While the Kelvin-Voigt (KV) representation of a soil captures the general viscous behavior using a dashpot, it fails to account for the possibly separate motions of the fluid and frame (there is only a single mass element). An alternative representation which separates the two masses, water and frame, is presented here. This Kelvin-Voigt-Maxwell-Biot (KVMB) model draws on elements of the long standing linear viscoelastic models in a way that connects the viscous damping to permeability and inertial mass coupling. A mathematical mapping between the KV and KVMB representations is derived and permits continued use of the KV model, while retaining an understanding of the separate mass motions.

The classic Kelvin-Voigt (KV) solid may be the most enduring and ubiquitous model used to represent the engineering behavior of soils. Examples of its application include compressibility and settlement (Das 1993), as well as the response of soils under impact (Roesset et al. 1994). The model also governs the analysis of standard soil tests, including consolidation ASTM-D2435, (ASTM 1996a) and resonant-column tests ASTM-D4015 (ASTM 1996b). The model also finds application in describing ground water flow through unconsolidated granular soils (Domenico and Schwartz 1990). The KV representation of a soil element places a dashpot, c, in parallel with the spring, k [see FIG. 18(a)]. This system, composed from a single element, is a single degree of freedom oscillator, and this is the basis for the analysis of the resonant column test. If this single degree of freedom element is joined with other similar elements, the result is a multi-degree of freedom system [FIG. 18(b)]. When enough elements are cascaded, the assemblage can represent the one-dimensional (1D) propagation of a shear, horizontally polarized (SH) wave.

A number of writers have represented the dashpot-spring combination in terms of other tractable components. In extending Terzaghi's original one-dimensional theory of consolidation to three dimensions, Biot (1941) makes reference to Terzaghi's rubber sponge analogy as a way to describe the response of a saturated soil to compression. Later, Biot's papers on wave propagation introduce the idea of representing the pores by small cylinders. The cylinder diameter became the key parameter needed to quantify permeability (Biot 1956a). Biot used the cylinder diameter to extend his theory to include turbulent flow beyond a defined transition frequency (Biot 1956b). Biot's later work includes a number of figures which represent the spring and dashpot in terms of frame stiffness and fluid-frame viscous damping. Examples may be found in Biot (1962b) and Biot (1962a). Similar descriptions can also be found in Gassmann (1951) with his "open" and "closed" systems being end members of permeable and impermeable cases. The choice of uniform, spherical grains (Gassman 1951), or cylindrical pores of the same uniform diameter (Biot 1956a) fall short of describing actual soils. Their value is in that such simplifications lead to a tractable analysis. For example, the capillary tube models of fluid flow through soils have been used to derive Darcy's law (Bear 1972).

In early resonant column studies, dry samples were evaluated (Hardin 1965). The resulting measurements were in conflict with the constant viscosity property of the KV model. In order to retain a viscous representation, an effective viscosity was proposed which varied inversely with frequency. This introduction of an "effective" viscosity has become widespread and integrated into engineering practice (Kramer 1996). The continued use of the concept is testimony to the strong appeal of the KV representation, even in cases where a viscous effect is not observed. Stoll (1985) demonstrated that the introduction of water into the pore spaces could lead to a classic viscous response, suggesting that a dense viscous fluid, such as water, is required. Stoll presented results on an Ottawa sand which demonstrated an increase in damping with frequency, but only for water saturated samples. In the case of dry samples, damping remained constant with frequency.

Inspired by Stoll's reports for saturated soil and the theoretical foundation of Biot (1962a), the author formulated the KVMB model. This model behaves very much like the KV model, but splits the mass into two parts, and is a rearrangement of the elements in series (similar to a Maxwell body). When relating this KVMB model to a saturated soil, porosity can be used to define the mass ratio (frame to pore fluid). The dashpot is an expression of the permeability which controls the relative motion between frame and pore fluid. Further, it is possible to mathematically map the KVMB model elements to those of the classic KV representation, and thus relate determinations of porosity and KV viscous damping to permeability.

KVMB Representation

A major limitation of the KV model is that the mass is treated as a single element. A two phase medium, like a saturated soil, can not be fully represented with the masses bundled in this way. The KVMB representation presented here separates the mass into pore fluid and solid frame components (according to porosity). Viscous damping is then due to the frictional losses resulting from the relative motion between fluid and frame. Frictional losses from this motion produces the "dashpot". The KVMB dashpot depends on permeability.

The KVMB elemental representation is shown in FIG. 19(a). As in the case of the classic KV model, there is a single dashpot and a single spring, but arranged in series (reminiscent of the Maxwell model). Also, we can view the system from either point of view, an oscillator (single element) or wave (assemblage of elements). The significant difference is the explicit separation of the water mass from the frame mass by the dashpot (Biot's influence). The dashpot controls the relative motion between the two mass components (fluid and frame), and this permits us to relate the dashpot to permeability.

Dampened Oscillator Points of View

Engineering practice has a significant investment in the KV model. Our very concept of viscous damping and damping ratio for an oscillator are uniquely bound to this single degree of freedom (SDOF) system. Therefore, it is useful to find a mathematical mapping between the KV and KVMB representations. Both models produce very similar behavior, but the KVMB model can relate that behavior to soil fluid-frame interaction in a more direct way. A mapping between the KV and the KVMB models can be achieved through a Gedanken Versuch (thought experiment). This is done by examining a single dampened oscillator element for both representations. The components are considered matched when the free response time histories are as close as possible. We consider the free response due to an initial condition consisting of a velocity impulse applied to either the frame mass (KVMB), or the single mass element (KV). The mapping is facilitated by decoupling the differential equations and relating two of the respective eigenvalues. Thus, it is possible to compute an equivalent KV dashpot from the permeability and degree of inertial mass coupling represented by the KVMB model.

Decoupling the KV Representation

The governing differential equation for the free response of the KV model corresponds to the well understood SDOF system $$m\ddot{u} + c\dot{u} + ku = 0 \tag{B1}$$

where mass motion is given by displacement, u, velocity, $\dot{u}$, and acceleration, $\ddot{u}$. This second order ordinary differential equation (ODE) can be recast as a coupled system of two first order ODEs, (Sadun 2001)

$$\frac{d}{dt}u = A_{kv} \cdot u \tag{B2}$$

$$\frac{d}{dt}u = \frac{d}{dt}\begin{bmatrix} u \\ \dot{u} \end{bmatrix} = \begin{bmatrix} 0 & 1 \\ -\frac{k}{m} & -\frac{c}{m} \end{bmatrix} \cdot \begin{bmatrix} u \\ \dot{u} \end{bmatrix} \tag{B3}$$

where u=displacement-velocity vector. In this autonomous form, we recognize an eigenvalue problem which can be diagonalized in a new basis given by the eigenvectors of matrix, $A_{kv}$. Eqs. (B1) and (B3) are equivalent, as are their solutions. In the specific case of an underdamped system, the solution is an exponentially decaying sinusoid. The eigenvalues of $A_{kv}$ are complex, the imaginary part giving the damped oscillation frequency, and the real part the exponential decay envelope of the solution. The analytic solution to Eq. (B3) is given as (Sadun 2001)

$$\begin{bmatrix} u(t) \\ \dot{u}(t) \end{bmatrix} = B_{kv} \cdot \begin{bmatrix} e^{\lambda_1 t} & 0 \\ 0 & e^{\lambda_2 t} \end{bmatrix} \cdot B_{kv}^{-1} \cdot \begin{bmatrix} u(0) \\ \dot{u}(0) \end{bmatrix} \tag{B4}$$

where the new, diagonalized basis is given by matrix, $B_{kv}$, the columns of which are the eigenvectors of $A_{kv}$. For our particular choice, the initial conditions are given by u(0)=0 and $\dot{u}(0)$=1. In the underdamped case, the eigenvalues $\lambda_i$ will be complex conjugates.

Decoupling the KVMB Representation

By similar reasoning, the KVMB model shown in FIG. 19(a) obeys the coupled governing differential equation $$\frac{d}{dt}u = A_{kvmb} \cdot u \tag{B5}$$

$$\frac{d}{dt}\begin{bmatrix} u_f \\ \dot{u}_f \\ u_w \end{bmatrix} = \begin{bmatrix} 0 & 1 & 0 \\ -\frac{k}{M_f} & -\frac{d}{M_f} & +\frac{d}{M_f} \\ 0 & +\frac{d}{M_w} & -\frac{d}{M_w} \end{bmatrix} \cdot \begin{bmatrix} u_f \\ \dot{u}_f \\ u_w \end{bmatrix} \tag{B6}$$

Where $u_f$=frame-mass displacement; $\dot{u}_f$=frame-mass velocity; and $\dot{u}_w$=water-mass velocity. This 2DOF system is 3×3 with three eigenvalues. The solution giving the free response of the KVMB system to initial conditions is $$\begin{bmatrix} u_f(t) \\ \dot{u}_f(t) \\ \dot{u}_w(t) \end{bmatrix} = B_{kvmb} \cdot \begin{bmatrix} e^{\gamma_1 t} & 0 & 0 \\ 0 & e^{\gamma_2 t} & 0 \\ 0 & 0 & e^{\gamma_3 t} \end{bmatrix} \cdot B_{kvmb}^{-1} \cdot \begin{bmatrix} u_f(0) \\ \dot{u}_f(0) \\ \dot{u}_w(0) \end{bmatrix} \tag{B7}$$

Where are three eigenvalues, $\gamma_i$, and the columns of the new basis matrix, $B_{kvmb}$, are the eigenvectors of $A_{kvmb}$. Our choice of initial conditions is $u_f(0)$=(0), $\dot{u}_f(0)$=1, and $\dot{u}_w(0)$=0. In both the KV and KVMB cases, the single mass, or the frame mass receives an initial velocity impulse, respectively. For an underdamped system, Eq. (B7) is an exponentially decaying sinusoid superimposed on an exponentially decaying trend. This superimposed trend is small in amplitude, and thus the two models can be effectively mapped.

Motivation for Mapping KV to KVMB

The advantage of the KVMB system lies in its separation of the two mass components, solid, and water. Once the masses are separated, the viscous damping may be related to the permeability. Motivation for the mapping resides in the existing laboratory and field methods which are grounded in the KV model. We can relate the laboratory or field measured spring and dashpot values (KV model) to corresponding values for the KVMB spring and dashpot. Assuming porosity is known, the resultant KVMB dashpot can be related to the soil permeability, producing a technique to evaluate permeability from either resonant column or SH wave determinations of damping (Michaels 1998—as in Example A).

An intuitive description of the mapping is as follows. At one end limit, say in a clay, the pore fluids move largely with the frame, the lack of significant relative motion leading to small damping values. We say that the masses are coupled in a clay, and the KVMB dashpot would have a large value (but the KV dashpot would be small in value). At the other extreme, say a gravel with large pores, the pore fluids and frame move independently. We say that the masses are uncoupled in a gravel, and the KVMB dashpot has a small value (as does the KV dashpot). The frictional losses are small due to the large pore diameters.

Between these two extremes, say for a sand, the permeability is small enough to maximize viscous friction and hence damping. That is, the pores are large enough to permit significant relative motion between the pore fluid and frame, but small enough to lead to significant viscous friction and damping. Intuitively, we expect a peak in equivalent KV damping value to occur at the transition between coupled and uncoupled cases.

Experimental support for the view that viscous damping is related to fluid-frame interaction in sands is found in Stoll (1985). Stoll demonstrated that resonant column testing of saturated sands produces a frequency dependent damping, while dry samples produce a damping which is nearly frequency independent. In short, water can produce a larger viscous damping effect than air since the mass of water will be more than the mass of air for the same pore volume. Thus, when combined with porosity and pore fluid specifications, the KVMB representation is able to predict both the large and small viscous effects corresponding to saturated and dry conditions, respectively.

Mapping KV and KVMB Representations

As previously mentioned, the mapping is done through the thought experiment. Each dampened oscillator, KV and KVMB, is excited by a velocity impulse applied to the combined or frame mass, respectively. We consider the spring and dashpot components of the two alternative models mapped when the resultant free response of the frame mass (KVMB) is as close as possible to the response of the combined mass (KV). We can view the response of each system as a time series describing the position of the mass as a function of time. For the KVMB model, this would be the frame mass, for the KV model the combined mass.

A scalar metric which quantifies the similarity between these two displacement signals is given by the angle between the two time series. The angle is $$\theta = \arccos\left(\frac{u_f^T \cdot u}{\|u_f\| \cdot \|u\|}\right) \quad (B8)$$

where $u_f$=displacement time history of the solid frame mass of the KVMB model; and u=displacement of the combined mass in the KV model. The denominator terms are the Euclidean (L2) norms for the two signals. Because both signals are essentially exponentially decaying sinusoids, there is no need to consider the response beyond the point where the motion has died out. The angle θ provides a scalar metric which can be used to evaluate the mapping between the two representations. The smaller the value of θ, the better the match. Thus, if the two time histories were identical, the angle would be zero. In the author's experience, values of θ less than 5 correspond to time histories which are virtually indistinguishable.

The solution is to discard the purely real eigenvalue of the KVMB system, and retain only the complex-conjugate eigenvalue pair. It is the complex-conjugate pair which produce that part of the response associated with the KV model. The retained KVMB eigenvalues are substituted into the KV solution which gives the eigenvalues in terms of the spring and dashpot constants. One simply back solves for the component values from the eigenvalues. The solution is to set $\lambda_1=\gamma_1$, $\lambda_2=\gamma_2$, discard $\gamma_3$, and $$\frac{k}{m} = \lambda_1 \cdot \lambda_2 \quad (B9)$$

$$\frac{c}{m} = -(\lambda_1 + \lambda_2) \quad (B10)$$

Where $\gamma_1$ and $\gamma_2$=retained complex conjugate eigenvalues from the KVMB representation; and m=KV mass which effectively completes the mapping. Thus, it is not necessary to actually compute the time series contemplated in the thought experiment. We need only determine the KVMB eigenvalues to compute the effective spring-mass and dashpot-mass ratios of the KV system. Note that we obtain only ratios with respect to mass on the left hand side, not individual values for the spring and dashpot. It is these ratios that determine the eigenvalues of the KV system given in equation Eq. (B3).

FIG. 20 illustrates the mapping for a specific KVMB oscillator. Here, values of frame mass (1,000 kg) and frame spring (1E+8 N/m) were held constant while the KVMB dashpot value varied over a range from 10 to $10^9$ kg/s. Two cases of water mass are shown and indicated by the ratio of frame to fluid masses. The case where the water and frame masses are equal is shown as a solid curve.

FIG. 20(a) shows the mapped equivalent dashpot for the KV model. At low values of damping, the KV and KVMB dashpots are equal (similar to what we would expect for a very permeable soil, like a gravel). The equivalent spring stiffness is shown in FIG. 20(b). The KVMB and KV stiffness values are also equal at low KVMB damping values. As the KVMB damping value increases, we reach a peak in the effective KV dashpot. This marks the transition point where the water and the frame begin to move together. Beyond the peak, the motion becomes increasingly coupled, and due to the reduced relative motion between frame and water, we have less friction and less equivalent damping. In terms of a soil, a large KVMB damping would represent a clay or other soil of low permeability. The water, being dragged in the pores, reduces the frictional losses. Further, with the two masses largely moving together, we expect a reduction in the resonant frequency of the moving frame. This predicted reduction in natural frequency is expressed as an apparent reduction in the KV stiffness (since the frame mass is constant). In this example, the natural frequency of the oscillator drops from about 50 to 35 Hz.

Normalization to Damping Ratio

While the above example is for a specific mass, spring and dashpot, we can view the problem from a normalized, general point of view. We do this by modifying the damping plot shown in FIG. 20(a), replacing damping values with damping ratios. There are two damping ratios to be considered (KV and KVMB). Although the formulas are identical, the ratios correspond to different arrangements of the elements. The formula for damping ratio is well known, and is given by $$\xi = \frac{C}{2\sqrt{K \cdot M}} \quad (B11)$$

where C=dashpot's viscous damping (kilograms/second); K=spring's stiffness (Newtons/meter), and M=mass (kilograms). Damping ratio, ξ, is unitless. The dashpot and spring require no comment for either the KV or KVMB models. The mass does require some thought, since there are two of them in one model, and one mass in the other. Since the left hand side of Eqs. (B9) and (B10) are ratios, we can eliminate the mass in computing the equivalent KV damping ratio of Eq. (B11). The resulting expression for the KV damping ratio in terms of the complex conjugate eigenvalues taken from the KVMB system is $$\xi = \frac{\sqrt{(\lambda_1 + \lambda_2)^2}}{2\sqrt{\lambda_1 \lambda_2}} = \frac{|\lambda_1 + \lambda_2|}{2\sqrt{\lambda_1 \lambda_2}} \tag{B12}$$

On the other hand, there is no single correct answer for which KVMB mass to employ in Eq. (B11). Two choices are the sum of the water and frame masses, or the frame mass alone. The former makes sense for coupled motion, the later for uncoupled. Fortunately, for porosities likely to be encountered in most soils, the difference between these two options will be small. In this paper, the combined mass of water plus frame has been used to compute the KVMB damping ratio.

FIG. 21 shows the equivalent KV damping ratio as a function of the KVMB damping ratio. Curves are shown for different mass ratios between the frame and water. Note that as the fluid mass declines (larger mass ratio), the curve maximum shifts down and to the left. A decrease in mass ratio would correspond to a decline in porosity for a soil. It also suggests that replacing water with a less dense fluid (say air) will produce less viscous damping.

In the next section, the KVMB dashpot will be related to damping in the manner which Biot approached the problem, a capillary tube soil model. The partitioning of the frame and water masses will be based on porosity and the assumption of a saturated soil. The development is focused on describing shear motion and shear waves (not compressional waves).

Relating KVMB Damping to Permeability

We follow the model proposed by Biot (1956a) in his work on wave propagation. A pore is represented by a right-circular cylinder of diameter, $\delta$. The head loss, $h_f$, for fluid flow in the pore is then given by the Darcy-Weisbach equation $$h_f = \frac{fLv_s^2}{2\delta g} \tag{B13}$$

where L=pore length; $v_s$=specific flow velocity in the pore; g=acceleration due to gravity; and f=friction factor. We follow Biot's example, and assume laminar flow. Thus, we let the friction factor be given in the usual way $$f = \frac{64}{R} = \frac{64\mu}{\rho_w \delta v_s} \tag{B14}$$

Where R=Reynolds number; $\rho_w$=pore fluid density; and $\mu$=pore fluid dynamic viscosity (units of Pa/s). Substituting Eq. (B14) into Eq. (B13) we have $$h_f = \frac{32\mu L v_s}{\rho_w \delta^2 g} \tag{B15}$$

For an elemental volume of soil represented by a solid perforated by uniform, parallel, cylindrical pores, the net flow velocity out of a cross section including many pores is $$v = nv_s \tag{B16}$$

where n=porosity for the given volume. For our element of length L, and cross-sectional area, A, Darcy's equation is given by $$\frac{Q}{A} = v = K_d \left(\frac{h_f}{L}\right) \tag{B17}$$

where Q=volumetric flow rate; and $K_d$=hydraulic conductivity (units of meter/second). Equating the velocities, v, in Eqs. (B16) and (B17), we can solve for hydraulic conductivity in terms of pore size and the other model parameters $$k_d = \frac{n\rho_w \delta^2 g}{32\mu} \tag{B18}$$

This result is the same as that given by Bear (1972) (see p. 165). Bear made the point that the 32 in the denominator is "meaningless," and that some writers scale the 32 by a "tortuosity" factor which scales the representation to a real soil in which the pores are not parallel or cylindrical, and a diverse size of pores exist. This last point leads one to conclude that $\delta$ is meant to be an "effective" pore diameter, representative of the actual pore diameters. Essentially, multiplying 32 by a tortuosity only affects the relationship between $K_d$ and $\delta$.

Biot (1956a) gives a dissipation coefficient in his Eq. (6.8)

$$b = \frac{\mu n^2}{\bar{k}} \tag{B19}$$

where we have used the current notation for porosity. Biot refers to $\bar{k}$ as Darcy's coefficient of permeability. This is in fact the absolute permeability (units of meter$^2$), and is related to our hydraulic conductivity by $$\bar{k} = \frac{K_d \mu}{g\rho_w} \tag{B20}$$

Further, Biot's Eq. (7.11) gives b for cylindrical pores as $$b = \frac{32\mu n}{\delta^2} \tag{B21}$$

If we substitute Eq. (B20) into Eq. (B19), we obtain $$b = \frac{n^2 g \rho_w}{K_d} \tag{B22}$$

Substituting $K_d$ from Eq. (B18) into Eq. (B22), we obtain equation Eq. (B21), thus illustrating that our $K_d$ of Eq. (B18) is in exact agreement with Biot's paper, and his assumptions at low frequencies and laminar flow.

Biot's dissipation factor, b, is the coefficient of a term in his wave Eq. (6.7). That is, b=coefficient of the term which is the difference between the fluid and frame velocities. Thus, b plays the role of a dashpot connected between the frame and water masses of our FIG. 19(*a*). It is not, however, the lumped dashpot value. We note that b has units of kilogram/second per meter$^3$, while an ideal dashpot elements has units of kilograms/second. Biot's damping coefficient is to a dashpot damping value as density is to mass. To obtain the ideal, lumped, components (spring, dashpot, and mass), we need to integrate the specific properties over a common volume of material being represented.

Determining Spring, Mass, and Dashpot for a Volume

Consider an elemental volume of cross-sectional area, A, and length, L, as shown in FIG. 22. For a simple shear due to a traction F/A, and a frame material with shear modulus, $G_f$ we have $$g_f = \frac{\left(\frac{F}{A}\right)}{\left(\frac{\Delta x}{L}\right)} = \frac{\frac{k\Delta x}{A}}{\frac{\Delta x}{L}} = \frac{kL}{A} \quad (B23)$$

Solving for the spring constant, we have $$k = \frac{G_f A}{L} \quad (B24)$$

For our KVMB dashpot, we have $$d = bAL = \left(\frac{n^2 g \rho_w}{K_d}\right)(AL) \quad (B25)$$

The frame and water masses follow from porosity and the specific gravity of the solid, $G_s$.
They are respectively, $$m_f = AL(1-n)G_s\rho_w \quad (B26)$$

$$m_w = nAL\rho_w \quad (B27)$$

KV Damping Ratio Versus Hydraulic Conductivity

FIG. 23 illustrates the mapping at a single frequency, 50 Hz. In this thought experiment, we consider a single element of soil with length L. For a desired natural frequency, ω, we can determine the length of the required volume, L, stiffness-mass ratio as follows:

$$L^2 = \frac{G_f}{\omega^2(1-n)G_s\rho_w} \quad (B28)$$

where frequency, ω, is in rad/s. We can obtain the hydraulic conductivity by solving Eq. (25) for $K_d$ $$K_d = \frac{n^2 g \rho_w AL}{d} \quad (B29)$$

where the dashpot value, d, is varied over a range of values to produce FIG. 23. Curves are computed for selected porosity values of 10, 30, and 50%.

To emphasize the fact that two different coupling conditions may result in the same KV damping ratio, three points have been annotated in FIG. 23. Point A corresponds to maximum damping obtainable for a porosity of 30%. Point B corresponds to a largely coupled condition, and point C to a largely uncoupled condition which produce the same value of equivalent KV damping ratio (ξ=0.0135).

FIG. 24 gives the corresponding particle velocity time histories for the fluid and frame motions for the three cases indicated by A, B, and C in FIG. 23. For the point B case ($K_d$=0.002 m/s), the motions are closely coupled, and the particle velocities are almost together. The slight difference in velocity between frame and water results in an equivalent KV damping ratio of 0.0135. At the other extreme, case C, there is a significant difference in the frame and mass velocities. However, the equivalent KV damping ratio is only 0.0135 since the hydraulic conductivity is large ($K_d$=0.06 m/s). The point is that the combined larger velocity difference and larger effective pore diameter in case C results in the same frictional loss that results from smaller pore diameters with less relative velocity between fluid and frame. The maximum damping occurs at point A ($K_d$=0.0109 m/s), where the combined pore diameter and relative velocity difference produce a maximum in the viscous friction.

For the three cases shown in FIG. 24 the Eq. (B8) metric was computed to assess the match between the KV and KVMB displacement time histories. The largest difference (poorest match) was for point A, and resulted in an angle of θ=2.04°. If the two displacement time histories were to be plotted here, they would appear as one, making this an acceptable match. The best match was for point C (θ=0.036°). Point B matched with a metric of θ=1.47°.

KV Damping Ratio Versus Frequency

This final example illustrates the effect of frequency on the KV damping ratio. In this thought experiment, the porosity is held at 30%. The sample length was varied to produce a range of natural frequencies for the vibrating soil element.

FIG. 25 shows the equivalent KV damping ratio as a function of natural frequency for three cases of hydraulic conductivity (0.002, 0.0109, 0.060 m/s corresponding to B, A, and C of FIG. 23). At 50 Hz, points B and C plot at the same point, the intersection of the $K_d$=0.06 and $K_d$=0.002 m/s curves. Points B and C produce the same damping, but for the different reasons explained in the previous section (B is largely coupled, C is largely uncoupled motion between fluid and frame). FIG. 25 is simply another way of looking at the same situation. What is different in this view is the effect of frequency on the equivalent KV damping ratio. The theory predicts that at low frequencies (left of a curve's apex), the motion between fluid and frame is largely coupled. At high frequencies (right of a curve's apex), the motion is largely uncoupled. A crude analogy would be to consider a table with dishes resting on a tablecloth. The largely uncoupled, high-frequency case is analogous to a waiter snapping the tablecloth off a table without disturbing the dishes (large relative motion between tablecloth and dishes). The largely coupled, low-frequency case is analogous to slowly pulling on the tablecloth. The dishes would be dragged along with the tablecloth.

Conclusions

Example B

The (KV) model is widely employed in soil dynamics, consolidation theory, and ground water flow. While the KV dashpot represents the viscous interaction of pore fluids with frame, there is no allowance for separate motion between the fluid in frame (the masses are considered to be lumped together as a single unit). The KVMB model presented here permits the fluid and frame masses to have independent motion, and relates the dashpot connecting them to soil permeability. The two models (KV and KVMB) have been mapped through the eigenvalues of the decoupled differential equations, permitting the continued use of the KV model to be related to the KVMB and soil permeability (provided that porosity or void ratio is known).

The theory predicts the following:
1. For a given porosity, there will be a maximum KV damping (point A in FIG. 23 or 25). This is the point where the difference between KV and KVMB representations is largest, but always acceptable ($\theta \leq 5°$). It is the point where the combination of significant relative motion between fluid in frame combines with a medium pore size to maximize equivalent KV damping.
2. Below point A, there will be two theoretical cases which produce the same KV damping. One is a largely coupled condition (small pores, small relative velocity between frame and fluid), and the other is a largely uncoupled condition (large pores, larger relative velocity between frame and fluid). See points B and C of FIG. 23 for example.
3. At low frequencies, to the left of the KV damping ratio apex, the motion will be largely coupled.
4. At high frequencies, to the right of the KV damping ratio apex, the motion will be largely uncoupled.

Notation

Example B

The following symbols are used in this paper.
A=cross-sectional area of soil element in thought experiment ($m^2$);
b=Biot dissipation coefficient (kg/s $m^3$);
c=dashpot constant for KV model (kg/s);
d=dashpot constant for KVMB model (kg/s);
f=friction factor in a cylindrical pore (unitless);
$f_n$=natural cyclic frequency of soil element (Hz);
$G_f$=shear modulus of frame (Pa);
$G_s$=specific gravity of soil solids (unitless);
g=acceleration due to gravity (9.81 $m/s^2$);
$h_f$=head loss in a cylindrical pore (m);
$K_d$=hydraulic conductivity (m/s);
k=KV spring (N/m);
$\bar{k}$=absolute permeability $M^2$);
$k_f$=spring constant of frame (N/m);
L=length of soil element in thought experiment (m);
m=KV mass (kg);
$m_f$=frame mass for KVMB model (kg);
$m_w$=water mass for KVMB model (kg);
n=porosity (unitless);
R=Reynolds number for flow in a cylindrical pore (unitless);
t=time (s);
u=particle displacement of KV mass (m);
$\dot{u}$=particle velocity of KV mass (m/s);
$u_f$=particle displacement of frame in thought experiment (m);
$\dot{u}_f$=particle velocity of frame in thought experiment (m/s);
$\dot{u}_w$=particle velocity of water in thought experiment (m/s);
v=net flow velocity of fluids in a cross-section of pores (m/s);
$v_s$=specific flow velocity in pore (m/s);

$\gamma_1, \gamma_2, \gamma_3$=eigenvalues of KVMB representation;
$\delta$=pore diameter (m);
$\lambda_1, \lambda_2$=eigenvalues of KV representation (complex conjugate pair of KVMB);
$\mu$=absolute viscosity of pore fluids (Pa s);
$\xi$=damping ratio (unitless);
$\rho_{frame}$=mass density of frame (kg/m3);
$\rho_w$=mass density of water (1,000 $kg/m^3$); and
$\omega_n=2\pi f_n$ natural frequency of soil element in thought experiment (rad/s).

Example C

Programming Example

```
KD-4X.sci
clear
// P. Michaels<pm@cgiss.boisestate.edu> 14 Oct. 2006
// Copyright (c) 2006 Paul Michaels, all rights reserved
// KD-4X.sci Scilab 4.0 version Permeability Computation
// http://www.scilab.org/ Web page to obtain Scilab
//KVMB Damping ratio for a given dashpot function
function [delta,frequ]=KVMB(d1)
// ODE in matrix form
// d1=dashpot value kg/s
//x-frame; xdot-frame; xdot-fluid
// d1=KVMB dashpot value, delta=equiv. KV damping ratio
m1=Mw; //water mass
m2=Mf; //frame mass
A=[0 1 0; . . .
    -kf/m2 -d1/m2 d1/m2; . . .
    0 d1l/m1 -d1/m1];
[B,x]=spec(A);
//A=B*x*inv(B)
//eigenvalues from diagonal of x
for jj=1:3
lambda(jj)=x(jj,jj);
end //next jj
//frame natural frequency
fnf=sqrt(kf/m2); //rad/s
//select eigenvalues for frame component of motion
j=1;
jselect=zeros(2,1);
for jj=1:3
tst(jj)=abs(fnf-abs(imag(lambda(jj))));
end //next jj
target=min(tst);
for jj=1:3
if tst(jj)==target then
jselect(j)=jj;
j=j+1;
end //endif
end //next jj
lambda1=lambda(jselect(1));
lambda2=lambda(jselect(2));
// compute KV equivalent damping ratio from 2 eigenvalues
delta=real(abs(lambda1+lambda2)/(2*sqrt
(lambda1*lambda2)));
frequ=real(abs(imag(lambda2))/2/% pi);
endfunction
function [drv]=deriv(x)
//numerical derivative
ptrb=.1;
f1=KVMB(x-ptrb*x);
f2=KVMB(x+ptrb*x);
drv=(f2-f1)/(2*ptrb*x);
endfunction
```

```
function [x]=linesrch(dmin,dmax)
x1=dmin;
x2=dmax;
xm=(x2+x1)/2; //midpoint of bracket
tol=1.E-19;
Fm=deriv(xm);
j=0;
//bisection search
while abs(Fm)>tol & j<100,
j=j+1;
F1=deriv(x1);
Fm=deriv(xm)
F2=deriv(x2);
if sign(F1)==sign(Fm) then
x1=xm;
F1=Fm;
xm=(x2+x1)/2;
else
x2=xm;
F2=Fm;
xm=(x2+x1)/2;
end //endif
end //endwhile
if j==100
disp("line search failed"+string(jrec))
end
x=xm;
endfunction
//bracket determination function
function [da1,da2,db1,db2,dpeak]=bracket(dmin,dmax)
//find peak damping ratio
dpeak=linesrch(dmin,dmax);
da1=dmin;
da2=dpeak;
db1=dpeak;
db2=dmax;
endfunction
//define inline objective functon for bisection search
function [F]=objf(d)
//d=KVMB dashpot value, drKv is observed KV damping ratio
[delta,frequ]=KVMB(d);
F=delta-drKV;
endfunction
function [x]=bisec(x1,x2)
xm=(x2+x1)/2; //midpoint of bracket
tol=0.0000001;
Fm=objf(xm);
j=0;
//bisection search
while abs(Fm)>tol & j<100,
j=j+1;
F1=objf(x1);
Fm=objf(xm)
F2=objf(x2);
if sign(F1)==sign(Fm) then
x1=xm;
F1=Fm;
xm=(x2+x1)/2;
else
x2=xm;
F2=Fm;
xm=(x2+x1)/2;
end //endif
end //endwhile
if j~=100
x=xm;
else
x=-1;
end
endfunction
//-------start of program-----------
nmn=input('enter well name, 2char', 's');
fname=nmn+"porsm5.dat";
//fname="x5porsm5.dat";
fp1=file('open', fname, 'old');
data=read(fp1,-1,3);
[nrow,ncol]=size(data);
for jrec=1:nrow
//elevation of sample convert to meters
elev(jrec)=data(jrec,2)*0.3048;
por(jrec)=data(jrec,3); //sample porosity
end //next jrec
file('close',fp1);
N=nrow; //save number of porosity values
meanpor=mean(por); //average porosity (entire log)
stdpor=stdev(por); //stdev porosity (entire log)
PorE=1.96*stdpor; //95% conf normal dist porosity
fname="casol.dat";
fp2=file('open',fname,'old');
casol=read(fp2,-1,9);
file('closet,fp2);
[nrow,ncol]=size(casol);
C1=casol(:,1); //stiffness
C2=casol(:,2); //damping
weight=casol(:,8); balance=casol(:,9);
C1E=casol(:,3); //stdev c1
C2E=casol(:,4); //stdev c2
C1E=1.96*C1E; //95% conf normal dist.
C2E=1.96*C2E; //95% conf normal dist.
[emin,kmin]=min(elev);
[emax,kmax]=max(elev);
txt1=['SDF Frequency Hz','BVAS Emax','BVAS Emin'];
EMX=sprintf("%.1f",emax);
EMN=sprintf("%.1f",emin);
sig=evstr(x_mdialog('Enter  Parameters',txt1['12';EMX;EMN]));
if length(sig)<3 then abort; end //user pressed cancel
//user selected resonator frequency for mapping
freqdr=sig(1);
uemin=sig(3); //user selected min elev
uemax=sig(2); //user selected max elev
//find min and max elevations
dfm=abs(elev-uemin);
dfx=abs(elev-uemax);
[ea,jmax]=min(dfm);
[eb,jmin]=min(dfx);
// convert frequency to radians/s, compute L=length resonator
wdr=freqdr*2*% pi; // radian frequency for damping ratio
L=sqrt(C1)/wdr; //length of vibrator
dratioKV=(wdr*C2)/(2*C1); // damping ratio
// error bar on KV dratio
t1=C1E**2;
t2=wdr**2;
t4=C2**2;
t5=C1**2;
t6=t5**2;
t10=C2E*2;
sigmadr=sqrt(t1*t2*t4/t6+t10*t2/t5)/2;
//compute mean porosity in user selected interval
umeanpor=mean(por(jmin:jmax));  //average porosity
ustdpor=stdev(por(jmin:jmax));   //stdev porosity
uPorE=1.96*ustdpor; //95% conf normal dist porosity uelev=
(uemin+uemax)/2; //elevation of user selected interval
```

```
//------------Compute Permeability------------------
A=1; // area of vibrator in meters^2
rhow=1000; //mass density of water
Gs=2.67; //specific gravity of solids
L=sqrt(C1)/wdr; //length of vibrator
//KVMB Model
Mf=(1-umeanpor)*Gs*rhow*A*L; //mass of frame
Mw=umeanpor*rhow*A*L; //mass of water
Mkv=Mf+Mw; //KV mass, coupled
kf=(C1*Mkv)/(L*L); //spring
fHZ=sqrt(kf/Mkv)/(% pi*2); //frequency implied (Hz)
//--------------------KVMB Analysis----------------------
//set up bracket for search
drKV=dratioKV;
KDmax=100; // max permeability m/s
KDmin=1.E-6; // min permeability m/s
dmax=(A*L*rhow*9.81*umeanpor^2)/KDmin;     //lower bound dashpot
dmin=(A*L*rhow*9.81*umeanpor^2)/KDmax;     //upper bound dashpot
//find brackets, coupled and uncoupled search
    [da1,da2,db1,db2,dpeak]=bracket(dmin,dmax);
    tst=KVMB(dpeak); //apex of curve=KVMB(da2)=KVMB(db1)
    drpksv=tst;
    if drKV>tst then
    KDa=0;
    KDb=0;
    drasv=0;
    drbsv=0;
    sigmaKDb=0;
    sigmaKDa=0;
    else
//do bisection search
    [xa]=bisec(da1,da2);
    dr=KVMB(xa);
    if xa==-1 then dr=-1; end
    drasv=dr;
    tmp1=(A*L*rhow*9.81*umeanpor^2);
    KDa=tmp1/xa ; //permeability m/s
    tmp2=-tmp1/(xa*xa); //derivative of KDa wrt dashpot, xa
    tmp3=deriv(xa); //derivative of damping ratio wrt dashpot
//stdev for permeability, KDa
    sigmaKDa=sqrt((tmp2/tmp3)^2*sigmadr^2);
    [xb]=bisec(db1,db2);
    if xb==-1 then dr=-1; end
    dr=KVMB(xb);
    drbsv=dr;
    tmp1=(A*L*rhow*9.81*umeanpor^2);
    KDb=tmp1/xb ; //permeability m/s
    tmp2=-tmp1/(xb*xb); //derivative of KDb wrt dashpot, xb
    tmp3=deriv(xb); //derivative of damping ratio wrt dashpot
//stdev for permeability, KDb
    sigmaKDb=sqrt((tmp2/tmp3)^2*sigmadr^2);
end
    ELV=uelev;
fp3=file('open','kd4.out','unknown');
msg0=nmn+"SOLUTION (+/-95% conf)";
msg1=sprintf( ...
"Elevation=%.2f(m)   Freq=%.0f(Hz)   Resonator_L=%.2f (m)" ..., ELV,freqdr,L);
msg2=sprintf( ...
"Damping Ratios: Peak=%.6f Wave=%.6f (+/-%.5f)" ..., drpksv,dratioKV,sigmadr*1.96);
msg3=sprintf( ...
"Coupled   (b_case):   DRb=%.6f   KDb=%.5f(+/-%.4 fm/s)" ..., drbsv,KDb,sigmaKDb*1.96);
msg4=sprintf( ...
"UnCoupled  (a_case):  DRa=%.6f   KDa=%.5f(+/-%.4 fm/s)" ..., drasv,KDa,sigmaKDa*1.96);
msg5=sprintf( ...
"Porosity: mean=%.3f (+/-%.3f)",umeanpor,ustdpor*1.96);
msg6=sprintf( ...
"Elevation Range: %.2f to %.2f(m)",uemin,uemax);
msG=[msg0;msg1;msg2;msg3;msg4;msg5;msg6]x_message_modeless([msg0,msg1,msg2,msg3,msg4,msg5,msg6]);
write(fp3,MSG,'(a)');
file('close',fp3);
```

Therefore, as may be understood from the above disclosure and Examples, the invention may comprise methods, apparatus, and/or programming are disclosed for engineering solutions, for example, in the areas of production from oil wells, grouting for soil improvement, treatment of contaminated soils, production from water wells, and waste disposal in landfills, wherein permeability of a fluid through a saturated material is determined by measuring the dynamic response of that saturated material to shaking vibrations and/or shear wave propagation, and then mapping the dynamic response (preferably, viscoelastic stiffness and damping properties) to an invented model (called "KVMB") that yields the property of permeability. The preferred embodiments may use shear waves, inertial effects, and/or transmission effects, but preferably not compression, to force fluids through the pores. The mapping preferably predicts two possible mappings to permeability, coupled and uncoupled. Unlike prior art seismic methods known to the inventor, the methods of the preferred embodiments are both internally consistent and directly related to known laws of physics rather than dependent on empirical calibrations. In use, for example, one may use a porosity log (conventional neutron or sonic) and recordings of SH-waves to obtain damping ratio, followed by locating of the damping ratio on a KVMB map that depends on porosity, and choosing of one of the two possible permeabilities indicated by the mapping, wherein the best choice is typically the largely coupled case.

Although this invention has been described above with reference to particular means, materials and embodiments, it is to be understood that the invention is not limited to these disclosed particulars, but extends instead to all equivalents within the broad scope of the following claims.

The invention claimed is:

1. A method of determining permeability of liquid through a liquid-saturated solid material, the method comprising:

a) performing vibration testing of a sample of said liquid in said liquid-saturated solid material, wherein said vibration testing provides porosity of the sample, mass of the liquid, mass of the solid material, and a measured Kevin-Voigt (KV) damping ratio for the sample, wherein damping ratio and dashpot are related by equation (1):

$$\text{Damping ratio} = \text{Dashpot}/(2\sqrt{k \times m}) \tag{1},$$

wherein m=total mass of liquid and solid material, and k=stiffness defined by equation (2), $$k = (\text{shear modulus of solid material} \cdot A)/L \tag{2},$$

wherein A=cross-sectional area of said sample volume, and L=length of said sample volume;

b) Mapping multiple calculated Kelvin-Voigt-Maxwell-Biot (KVMB)-determined equivalent KV damping ratio versus multiple assumed trial KVMB-dashpots, by the steps of:

assuming multiple trial KVMB dashpot values d, and calculating the three eigenvalues corresponding to a decoupled version of equation (3) for each assumed trial KVMB dashpot value:

$$\frac{d}{dt}\begin{bmatrix} u_f \\ \dot{u}_f \\ \dot{u}_w \end{bmatrix} = \begin{bmatrix} 0 & 1 & 0 \\ -\frac{k}{M_f} & -\frac{d}{M_f} & +\frac{d}{M_f} \\ 0 & +\frac{d}{M_w} & -\frac{d}{M_w} \end{bmatrix} \cdot \begin{bmatrix} u_f \\ \dot{u}_f \\ \dot{u}_w \end{bmatrix}, \quad (3)$$

wherein $u_f$=solid-material-mass displacement, $\dot{u}_f$=solid-material-mass velocity, and $\dot{u}_w$=liquid-mass velocity, $M_f$=mass of said solid material, $M_w$=mass of said liquid, and d=assumed trial KVMB dashpot value, and wherein k is defined by equation (2);

retaining two complex conjugate eigenvalues $\lambda_1$ and $\lambda_2$ of said three eigenvalues of said decoupled version of equation (3) for each assumed trial KVMB dashpot, inserting said two complex conjugate eigenvaluves into equation (4) to compute a KVMB-determined equivalent KV damping ratio ξ, and discarding the third of said three eigenvalues:

$$\xi = \frac{\sqrt{(\lambda_1+\lambda_2)^2}}{2\sqrt{\lambda_1\lambda_2}} = \frac{|\lambda_1+\lambda_2|}{2\sqrt{\lambda_1\lambda_2}}; \quad (4)$$

mapping said KVMB-determined equivalent KV damping ratios ξ versus the multiple assumed trial KVMB dashpots, determining the KVMB-determined equivalent KV damping ratio that most-closely matches the observed KV damping ratio and determining from said mapping a coupled KVMB dashpot solution and an uncoupled KVMB dashpot solution for said most-closely matched KVMB-determined equivalent KV damping ratio;

c) computing permeability $K_d$ of said liquid through said liquid-saturated solid material by inserting said coupled KVMB dashpot solution into equation (5):

$$K_d = \frac{n^2 g \rho_{liquid} A \cdot L}{d}, \quad (5)$$

wherein n=said porosity, g=acceleration due to gravity, $\rho_{liquid}$=mass density of said liquid, d=said coupled KVMB dashpot solution, A=cross-sectional area of said sample volume, and L=length of said sample volume.

2. A method as in claim 1, wherein said mapping multiple calculated Kelvin-Voigt-Maxwell-Biot (KVMB)-determined equivalent KV damping ratio versus multiple assumed trial KVMB-dashpots is performed by a bisection search.

3. A method as in claim 1, wherein said mapping provides a curve of calculated Kelvin-Voigt-Maxwell-Biot (KVMB)-determined equivalent KV damping ratio versus assumed trial KVMB-dashpot, and said curve is a downwardly-concave curved with a peak between said coupled KVMB dashpot solution and said uncoupled KVMB dashpot solution.

4. A method as in claim 1, wherein said performing vibration testing of a sample of said liquid in said liquid-saturated solid material is done in a field experiment.

5. A method as in claim 1, wherein said performing vibration testing of a sample of said liquid in said liquid-saturated solid material is done in a laboratory experiment.

6. A method as in claim 1, wherein cross-sectional area of said sample volume A is an assumed cross-sectional area.

7. A method as in claim 1, wherein cross-sectional area of said sample volume A is set at unity.

8. A method of determining permeability of liquid through a liquid-saturated solid material, the method comprising:
a) performing a shear-wave propagation testing survey of a sample volume of said liquid in said liquid-saturated solid material, wherein said survey provides an observed KV damping ratio by equation (1):

$$KV \text{ damping ratio} = \frac{\omega \cdot C_2}{2 \cdot C_1}, \quad (1)$$

at an angular frequency ω (rad/s) within the seismic source frequency band, stiffness $C_1$ (m²/s²), and damping $C_2$ (m²/s), all determined from shear-wave velocity dispersion and spatial propagation amplitude decay of said shear-wave propagation testing survey under the governing 1-D wave equation (2):

$$\frac{\partial^2 u}{\partial t^2} = C_1 \frac{\partial^2 u}{\partial x^2} + C_2 \frac{\partial^3 u}{\partial t^2}, \quad (2)$$

wherein u is particle displacement, x is spatial coordinate of wave propagation direction, and t is time;
b) computing a volume length L by equation (3):

$$L = \frac{\sqrt{C_1}}{\omega}; \quad (3)$$

c) laboratory testing of said sample volume to determine specific gravity of said solid material $G_{solids}$, and mass density of said saturated liquid $\rho_{liquid}$, and said sample volume porosity n;
d) Mapping multiple calculated Kelvin-Voigt-Maxwell-Biot (KVMB)-determined equivalent KV damping ratio versus multiple assumed trial KVMB-dashpots, by the steps of:
assuming multiple trial KVMB dashpot values, d, and calculating the three eigenvalues corresponding to a decoupled version of equation (4) for each assumed trial KVMB dashpot value:

$$\frac{d}{dt}\begin{bmatrix} u_f \\ \dot{u}_f \\ \dot{u}_w \end{bmatrix} = \begin{bmatrix} 0 & 1 & 0 \\ -\frac{k}{M_f} & -\frac{d}{M_f} & +\frac{d}{M_f} \\ 0 & +\frac{d}{M_w} & -\frac{d}{M_w} \end{bmatrix} \cdot \begin{bmatrix} u_f \\ \dot{u}_f \\ \dot{u}_w \end{bmatrix}, \quad (4)$$

wherein $u_f$=solid-material-mass displacement, $\dot{u}_f$=solid-material-mass velocity, and $\dot{u}_w$=liquid-mass velocity, $M_f$=mass of said solid material, $M_w$=mass of said liquid, and d=assumed trial KVMB dashpot value, and wherein k is defined by equation (5):

$$k=(\text{shear modulus of solid material} \cdot A)/L \quad (5),$$

wherein A=cross-sectional area of said sample volume, and L=length of said sample volume;

wherein $\mu_{solid}$ is the shear modulus of the solid material, $\rho_{solid}$ is the mass density of the solid material, and $\rho_w$ is the mass density of water;

retaining two complex conjugate eigenvalues $\lambda_1$ and $\lambda_2$ of said three eigenvalues of said decoupled version of equation (4) for each assumed trial KVMB dashpot, inserting said two complex conjugate eigenvaluves into equation (6) to compute a KVMB-determined equivalent KV damping ratio $\xi$, and discarding the third of said three eigenvalues:

$$\xi = \frac{\sqrt{(\lambda_1 + \lambda_2)^2}}{2\sqrt{\lambda_1 \lambda_2}} = \frac{|\lambda_1 + \lambda_2|}{2\sqrt{\lambda_1 \lambda_2}}; \qquad (6)$$

mapping said KVMB-determined equivalent KV damping ratios $\xi$ versus the multiple assumed trial KVMB dashpots, determining the KVMB-determined equivalent KV damping ratio that most-closely matches the observed KV damping ratio and determining from said mapping a coupled KVMB dashpot solution and an uncoupled KVMB dashpot solution for said most-closely matched KVMB-determined equivalent KV damping ratio;

e) computing permeability $K_d$ of said liquid through said liquid-saturated solid material by inserting said coupled KVMB dashpot solution into equation (6):

$$K_d = \frac{n^2 g \rho_{liquid} A \cdot L}{d}, \qquad (6)$$

wherein n=said porosity, g=acceleration due to gravity, $\rho_{liquid}$=mass density of said liquid, d=said coupled KVMB dashpot solution, A=cross-sectional area of said sample volume, and L=length of said sample volume.

9. A method as in claim 8, wherein said mapping multiple calculated Kelvin-Voigt-Maxwell-Biot (KVMB)-determined equivalent KV damping ratio versus multiple assumed trial KVMB-dashpots is performed by a bisection search.

10. A method as in claim 8, wherein said mapping provides a curve of calculated Kelvin-Voigt-Maxwell-Biot (KVMB)-determined equivalent KV damping ratio versus assumed trial KVMB-dashpot, and said curve is a downwardly-concave curved with a peak between said coupled KVMB dashpot solution and said uncoupled KVMB dashpot solution.

11. A method as in claim 8, wherein said performing vibration testing of a sample of said liquid in said liquid-saturated solid material is done in a field experiment.

12. A method as in claim 8, wherein said performing vibration testing of a sample of said liquid in said liquid-saturated solid material is done in a laboratory experiment.

13. A method as in claim 8, wherein cross-sectional area of said sample volume A is an assumed cross-sectional area.

14. A method as in claim 8, wherein cross-sectional area of said sample volume A is set at unity.

\* \* \* \* \*